(12) United States Patent
Sherman

(10) Patent No.: US 7,593,772 B2
(45) Date of Patent: Sep. 22, 2009

(54) METHODS AND DEVICES TO CHARACTERIZE THE PROBABILITY OF SUCCESSFUL DEFIBRILLATION AND DETERMINE TREATMENTS FOR VENTRICULAR FIBRILLATION

(76) Inventor: Lawrence Duane Sherman, 18544 NE. 19th Pl., Bellevue, WA (US) 98008

( * ) Notice: Subject to any disclaimer, the term of this patent is extended or adjusted under 35 U.S.C. 154(b) by 555 days.

(21) Appl. No.: 10/955,898

(22) Filed: Sep. 30, 2004

(65) Prior Publication Data
US 2005/0245973 A1 Nov. 3, 2005

Related U.S. Application Data

(60) Provisional application No. 60/521,465, filed on Apr. 30, 2004.

(51) Int. Cl.
*A61N 1/39* (2006.01)
(52) U.S. Cl. .......................... 607/5; 600/518
(58) Field of Classification Search ................ 607/5, 607/14, 4; 600/518
See application file for complete search history.

(56) References Cited

U.S. PATENT DOCUMENTS

| | | | | |
|---|---|---|---|---|
| 4,996,984 | A * | 3/1991 | Sweeney | 607/5 |
| 5,201,321 | A * | 4/1993 | Fulton | 600/515 |
| 5,480,413 | A * | 1/1996 | Greenhut et al. | 607/14 |
| 5,545,182 | A | 8/1996 | Stotts | |
| 5,683,424 | A | 11/1997 | Brown | |
| 5,755,671 | A * | 5/1998 | Albrecht et al. | 600/516 |
| 5,951,484 | A * | 9/1999 | Hoium et al. | 600/515 |
| 5,957,856 | A | 9/1999 | Weil | |
| 5,999,850 | A * | 12/1999 | Dawson et al. | 607/4 |
| 6,171,257 | B1 | 1/2001 | Weil | |
| 6,438,419 | B1 * | 8/2002 | Callaway et al. | 607/5 |
| 6,539,256 | B1 | 3/2003 | Kenknight | |
| 6,650,936 | B2 | 11/2003 | Sullivan | |
| 6,671,547 | B2 | 12/2003 | Lyster | |
| 6,760,621 | B2 | 7/2004 | Walcott | |
| 6,766,195 | B1 | 7/2004 | Bornzin | |
| 6,954,700 | B2 * | 10/2005 | Higashida et al. | 600/300 |
| 2004/0220489 | A1 * | 11/2004 | Sherman et al. | 600/518 |
| 2005/0137628 | A1 * | 6/2005 | Young et al. | 607/5 |

OTHER PUBLICATIONS

Watson, James N. et al., Improved prediction of defibrillation success for out of hospital VF cardiac arrest using wavelet transform methods. Resuscitation 63(2004)269-275.

* cited by examiner

*Primary Examiner*—George R Evanisko
*Assistant Examiner*—Joseph M Dietrich

(57) ABSTRACT

A computationally efficient method of determining the duration of ventricular fibrillation and the probability of successful defibrillation by analyzing an electrocardiogram using the logarithm of the absolute value of the autocorrelation function over a range of lags is disclosed. The method is particularly well suited for use in currently available defibrillators. The method is used in conjunction with frequency based measures, such as the angular velocity, to provide markedly improved accuracy in determining ventricular fibrillation duration, to indicate appropriate therapies to be delivered, and to assess the quality of ventricular fibrillation.

9 Claims, 8 Drawing Sheets

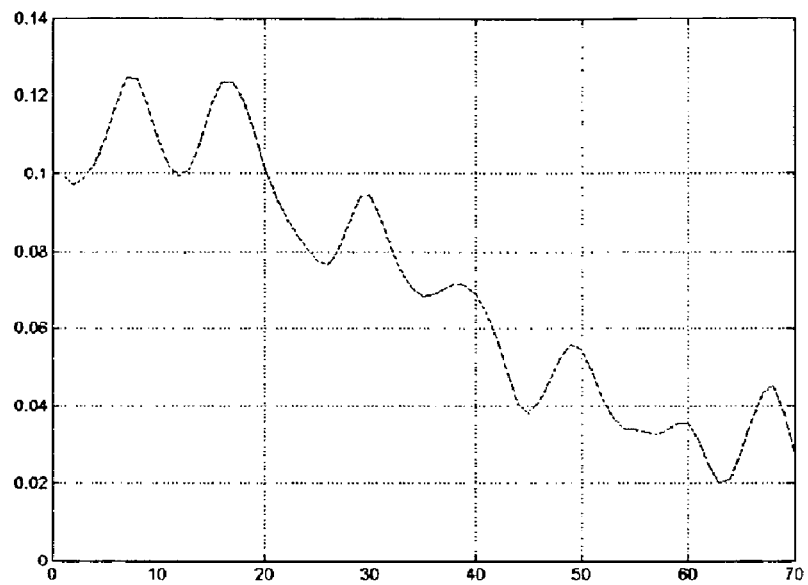
Figure 3    C1 cross-correlation with C2
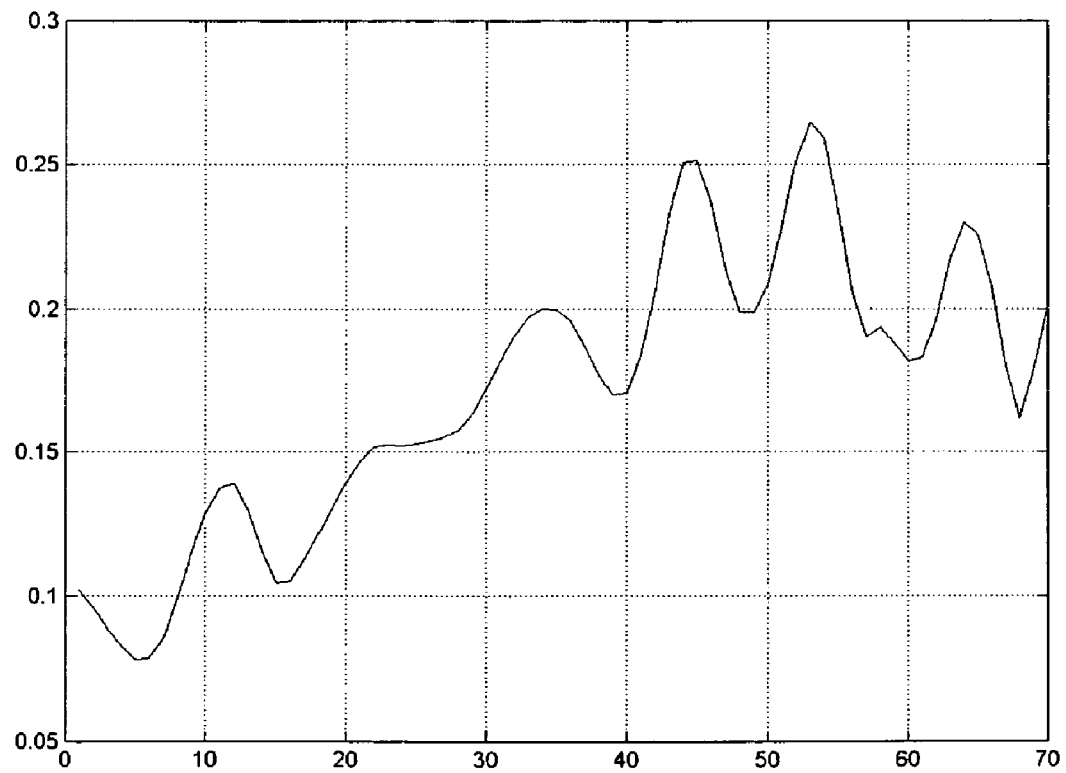
Figure 4    C2 Cross-correlation with C3

Figure 5     C3 Cross-correlation with C4
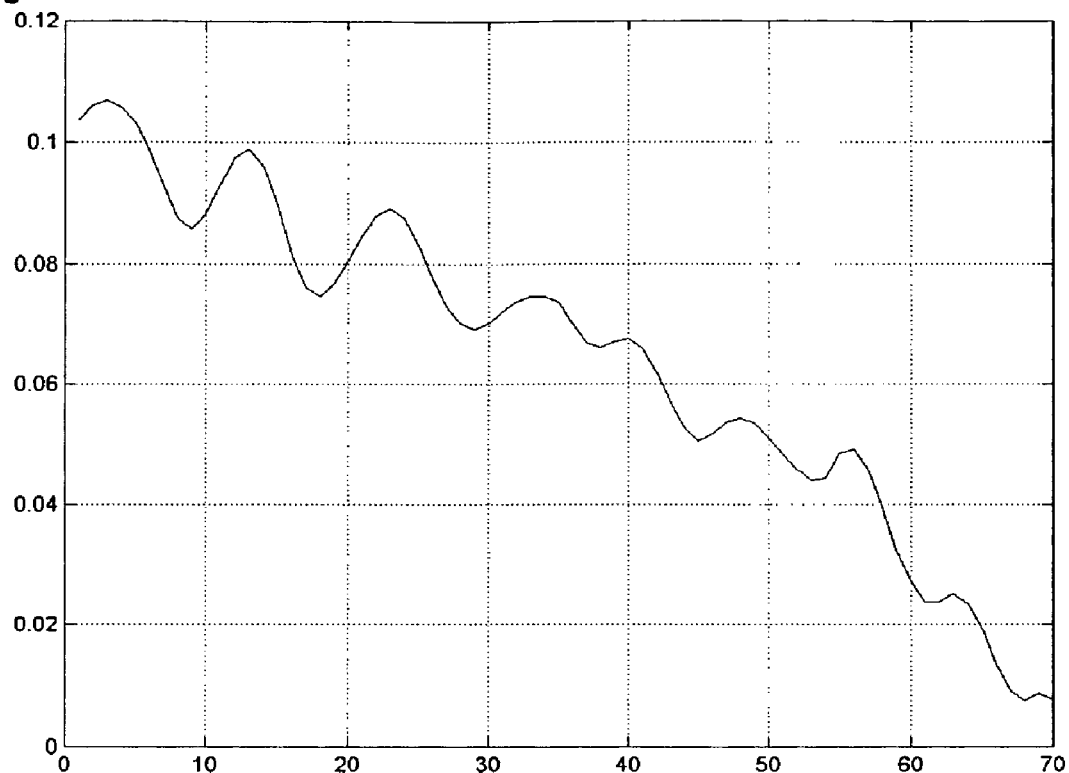
Figure 6    C4 Cross-correlation with C5
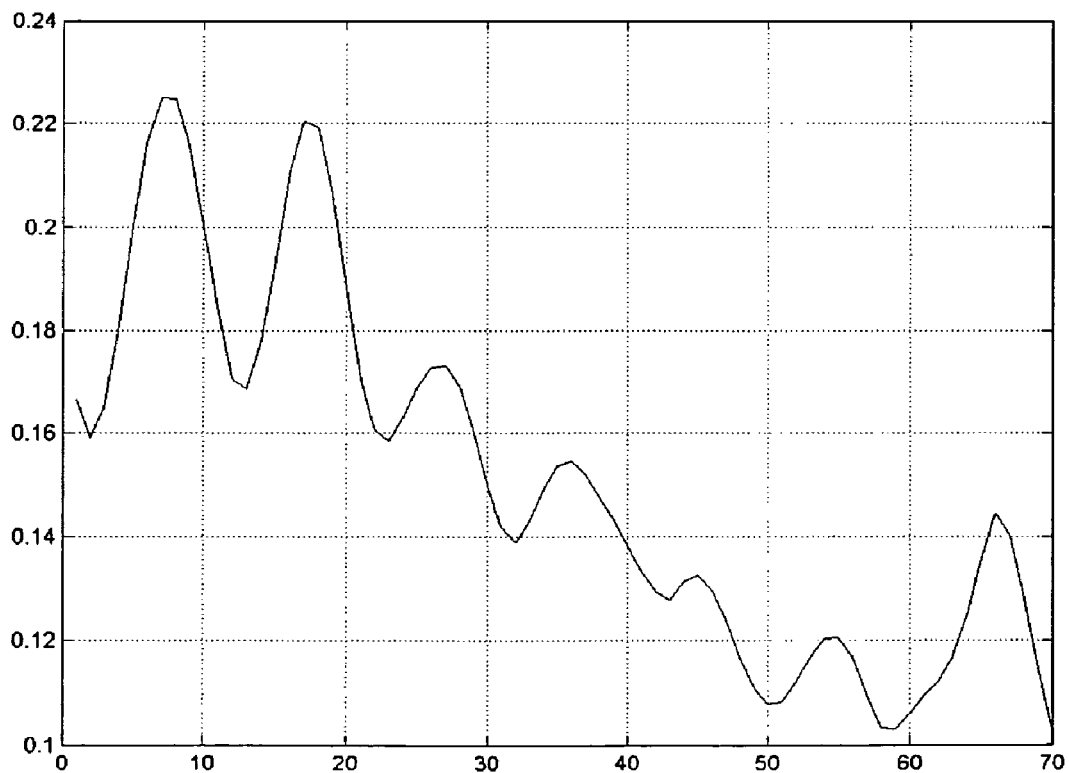

Figure 11
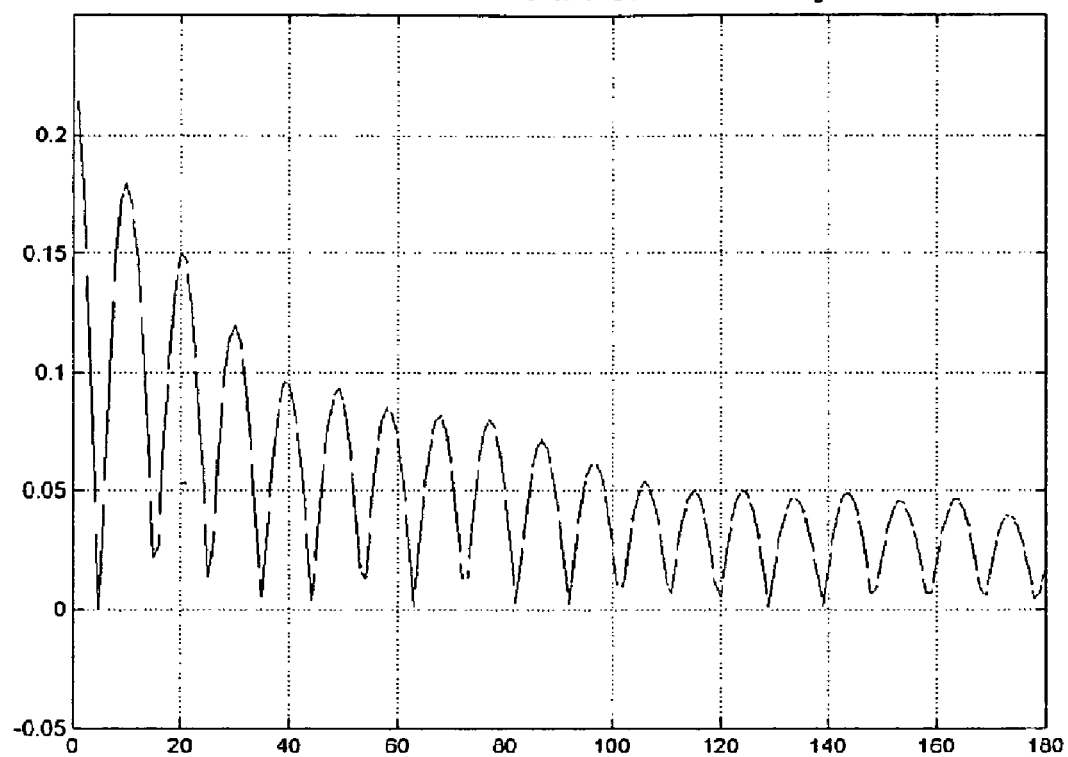
Absolute Value of Autocorrelation of ECG waveform in Figure 1
Figure 12 Cross-Correlation C4 and C5 without using Absolute Value of the ECG waveform prior to calculation
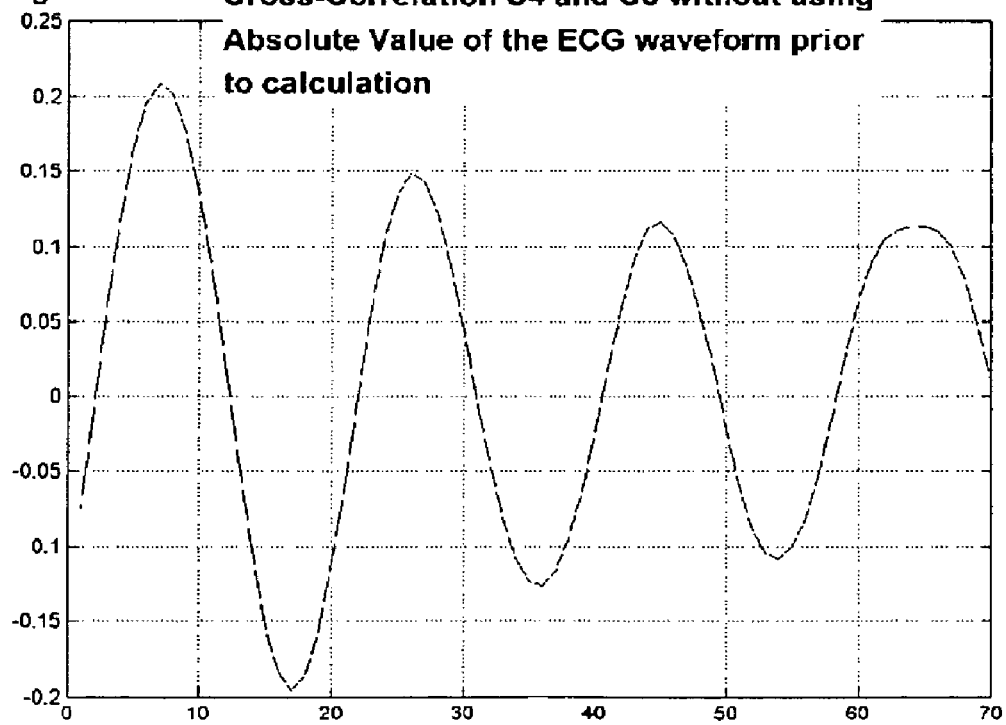

Fig. 13A — LAC/AV 1000 samples/sec

| | DISEASE | | |
|---|---|---|---|
| | VF<5 min | VF>5 min | |
| TEST VF<5 min | 1891 (TP) | 1085 (FP) | Positive Pred. Value 64% |
| VF>5 min | 208 (FN) | 2388 (TN) | Negative Pred. Value 92% |
| | 2099 TOTAL < 5 min | 3473 TOTAL > 5 min | 5572 TOTAL OF ALL |
| | SENSITIVITY 90% | SPECIFICITY 69% | Pretest Probability 38% |

Fig. 13B — LAC/AV 62.5 samples/sec Filtered 31.25 Hz

| | DISEASE | | |
|---|---|---|---|
| | VF<5 min | VF>5 min | |
| TEST VF<5 min | 1846 (TP) | 882 (FP) | Positive Pred. Value 68% |
| VF>5 min | 205 (FN) | 2609 (TN) | Negative Pred. Value 93% |
| | 2051 TOTAL < 5 min | 3491 TOTAL > 5 min | 5542 TOTAL OF ALL |
| | SENSITIVITY 90% | SPECIFICITY 75% | Pretest Probability 33% |

FIG. 14A — ScE/AV 1000 samples/sec

| | DISEASE | | |
|---|---|---|---|
| TEST | VF<5 min | VF>5 min | |
| VF<5 min | 1850 (TP) | 714 (FP) | Positive Pred. Value 72% |
| VF>5 min | 197 (FN) | 2086 (TN) | Negative Pred. Value 91.4% |
| | 2047 TOTAL < 5 min | 2800 TOTAL > 5 min | 4847 TOTAL OF ALL |
| | SENSITIVITY 90.4% | SPECIFICITY 74.5% | Pretest Probability 42.2% |

Fig. 14B — ScE/AV 62.5 samples/sec Filtered 31.25 Hz

| | DISEASE | | |
|---|---|---|---|
| TEST | VF<5 min | VF>5 min | |
| VF<5 min | 1846 (TP) | 1246 (FP) | Positive Pred. Value 60% |
| VF>5 min | 205 (FN) | 2245 (TN) | Negative Pred. Value 92% |
| | 2051 TOTAL < 5 min | 3491 TOTAL > 5 min | 5542 TOTAL OF ALL |
| | SENSITIVITY 90% | SPECIFICITY 64% | Pretest Probability 33% |

METHODS AND DEVICES TO CHARACTERIZE THE PROBABILITY OF SUCCESSFUL DEFIBRILLATION AND DETERMINE TREATMENTS FOR VENTRICULAR FIBRILLATION

CROSS-REFERENCE TO RELATED APPLICATIONS

This application claims the benefit of U.S. Provisional Patent Application Ser. No. 60/521,465, filed Apr. 30, 2004, the disclosure of which is incorporated herein as reference.

BACKGROUND OF THE INVENTION

1. Field of the Invention

The present invention is directed to methods and devices for the characterization of cardiac rhythms and, particularly, characterization of ventricular fibrillation and to methods and devices to be used in the treatment of ventricular fibrillation based upon the characterization of ventricular fibrillation.

References set forth herein may facilitate understanding of the present invention or the background of the present invention. Inclusion of a reference herein is not intended to and does not constitute an admission that the reference is available as prior art with respect to the present invention.

2. Prior Art

Ventricular Fibrillation (VF) is an abnormal and chaotic heart rhythm that results in death if not terminated within a short time period, generally accepted as less than 10 to 20 minutes. If cardiopulmonary resuscitation is applied, this interval maybe extended to as much as 30 minutes on rare occasions. There are an estimated 350,000 cardiac arrests which occur each year in the United States. VF is present in approximately 40% of these non-traumatic sudden death events. See Homberg, M, et al., "Incidence, duration and survival of ventricular fibrillation in out-of-hospital cardiac arrest patients in Sweden," Resuscitation, 44(1):7-17, 2000; and Cobb, L, et al., "Changing incidence of out-of-hospital ventricular fibrillation," 1980-2000, JAMA, 288(23):3008-13, 2000.

Ventricular Fibrillation is terminated by the application of an electric shock. It has become clear that this shock is most successful when delivered in the first 4-5 minutes of VF. It has also become evident that in patients in whom VF has persisted for more than 4-5 minutes, if CPR is performed before defibrillation is attempted, survival increases significantly. In a study of CPR for 90 seconds prior to defibrillation, there was a demonstrated increase in survival from 17% to 27% among patients given CPR prior to defibrillation when the response times were over four minutes, see Cobb, L A, et al., "Influence of cardiopulmonary resuscitation prior to defibrillation in patients with out-of-hospital ventricular fibrillation," JAMA, 281(13):1182-8, 1999.

In a second study, see Wik, L, et al., "Delaying defibrillation to give basic cardiopulmonary resuscitation to patients with out-of-hospital ventricular fibrillation," JAMA, 289(11): 1389-95, 2003, patients who had ambulance response times of over 5 minutes (indicating a duration of VF of 5 minutes or longer) demonstrated an increase in survival from 4% to 22% when 3 minutes of CPR was done prior to defibrillation attempts.

Since attempting defibrillation with an electric shock prior to giving CPR results in a decreased survival rate, it may be concluded that defibrillation is detrimental if given as the initial treatment in prolonged ventricular fibrillation of over 5 minutes duration. In these patients CPR should be performed first and in some cases the administration of medications and other therapies prior to defibrillation attempts may also increase survival rates.

Since it is usually impossible to objectively determine the duration of ventricular fibrillation accurately from the clinical situation (i.e. from bystanders) during the cardiac arrest event, prior art has focused on efforts to determine the duration and/or likelihood of successful defibrillation based on the examination of a short segment of the VF waveform. The duration of VF has been used as an estimator of the probability that defibrillation attempts will be successful. This is a well established marker and the probability of survival (as a result of successful defibrillation) is accepted as decreasing by approximately 10% for each minute that VF persists, see "American Heart Association in Collaboration with the International Liaison Committee on Resuscitation: Guidelines 2000 for Cardiopulmonary Resuscitation and Emergency Cardiovascular Care: An International Consensus on Science," Circulation 2000, 102(8)(Suppl. I) I -136-I-157 and see Callans, D J, "Out-of-hospital cardiac arrest-the solution is shocking," JAMA, 351(7):632-4, 2004.

Analysis of a short segment of ventricular fibrillation could, therefore, indicate two important features. Firstly, it could indicate the probability that an electric shock will result in the conversion of ventricular fibrillation to a perfusing, organized cardiac rhythm providing circulation to the patient. If this probability is high, such a shock should be immediately delivered. Secondly, it could indicate that the duration of ventricular fibrillation is longer than 4 or 5 minutes and/or that survival would be greatly improved if CPR, and perhaps other measures, were to be provided prior to a defibrillating shock. The prior art in this area has focused on various means to identify these two groups of patients based on the ECG waveform. Included in this reasoning is the consideration that a measure that is able to separate patients who would respond to electrical therapy from those that would not respond based on duration estimates would also be able to separate responders from non-responders even if the cause of the non-response was some other physiologic variable such as continued ischemia, metabolic derangements poisoning the myocardium, etc. In summary, a measure that is derived from studies based on duration estimates of ventricular fibrillation may also work well to estimate the overall physiology of the myocardium as it relates to probability of successful defibrillation by shock and/or probability of eventual survival.

It has been recognized for years that the roughness of the VF waveform seemed to correlate with the likelihood of successful defibrillation, however earlier efforts to quantify this observation have led to poor results. Prior efforts to quantify roughness based on amplitude have been unsuccessful because of many factors, including body habitus, electrode position, electrode conductance, myocardial mass, coexistent pulmonary disease, etc., See Weaver, W D, et al., "Amplitude of ventricular fibrillation waveform and outcome after cardiac arrest," Ann Intern Med, 102(1):53-5 1985; and Hargarten, K M, et al., "Prehospital experience with coarse ventricular fibrillation: a ten year review," Ann Emerg Med, 19(2):157-62 1990.

A number of subsequent attempts have focused on examining the underlying average frequency composition of the waveform as derived from Fourier analysis. See Dzwonczyk, R, et al., "The median frequency of the ECG during ventricular fibrillation: its use in an algorithm for estimating the duration of cardiac arrest," IEEE Trans Biomed Eng, 37:640-6 1990; Brown, C G and Dzwonszyk, R, "Signal analysis of the human electrocardiogram during ventricular fibrillation: frequency and amplitude parameters as predictors of successful countershock," Ann Emerg Med, 27(2): 184-8, 1996; and Berg, R A, et al., "Precountershock cardiopulmonary resuscitation improves ventricular fibrillation median frequency and myocardial readiness for successful defibrillation from prolonged ventricular fibrillation: a randomized, controlled swine study," Ann Emerg Med, 40(6): 563-70, 2002; U.S. Pat. Nos. 5,957,856 and 6,171,257. Such methods by themselves are poor predictors of ventricular fibrillation duration primarily because the median frequency and all frequency measures are multiphasic, exhibiting an initial increase to about 4 minutes, a decline through about 10 minutes and then a rise to time periods beyond 12 minutes, see Sherman, L D et al., "Angular velocity: a new method to improve prediction of ventricular fibrillation duration," Resuscitation, 60(1): 79-90, 2004. This makes a frequency in the middle range consistent with several different duration estimates.

Careful study of surface ECG waveforms during VF has led to the consideration that the apparently random activity may in fact be a manifestation of chaos. See, for example, Gray, R A, et al., "Spatial and temporal organization during cardiac fibrillation," Nature, 392:758 1998; Witkowski, F X, et al., "Spatiotemporal evolution of ventricular fibrillation," Nature, 392:78-82 1998; Witkowski, F X, et al., "Evidence for determinism in ventricular fibrillation", Phys Rev Lett, 75(6): 1230-3, 1995; Garfinkel, A, et al., "Quasiperiodicity and chaos in cardiac fibrillation," J Clin Invest, 99(2):305-14, 1997; and Hastings, H M, et al., "Nonlinear dynamics in ventricular fibrillation," Proc Natl Acad Sci USA, 93:10495-9, 1996.

Using methods derived from the fields of fractal geometry and nonlinear, chaotic dynamics, several studies addressed the problem of establishing the prior duration of VF in clinical and other settings through use of the scaling exponent (ScE), see Callaway, C W, et al., "Scaling structure of electrocardiographic waveform during prolonged ventricular fibrillation in swine," Pacing Clin Electrophysiol, 2:180-91, 2000; and Sherman, L D, et al., "Ventricular fibrillation exhibits dynamical properties and self-similarity," Resuscitation, 47(2):163-73, 2000; and Lightfoot et al., "Dynamic nature of electrocardiographic waveform predicts rescue shock outcome in porcine ventricular fibrillation," Ann Emerg Med, 42:230-241, 2003. The scaling exponent is a measure based on fractal geometry that measures the roughness of the VF waveform. It can be calculated in less than two seconds from a five-second surface recording of the ECG voltages. The scaling exponent has been found to increase over time from a low level of approximately 1.05 to a high level near 1.8 and provides a quantitative measure of the roughness of the VF waveform that is observed to change over time. The scaling exponent has also been shown to be predictive of the probability of successful defibrillation in patients treated with automated defibrillators see Callaway, C W, et al., "Scaling exponent predicts defibrillation success for out-of-hospital ventricular fibrillation cardiac arrest," Circulation, 103(12): 1656-61, 2001; and U.S. Pat. No. 6,438,419, the disclosures of which are incorporated herein by reference. Recently, the scaling exponent was used to evaluate the effect of performing initial immediate defibrillating shock versus starting resuscitation with CPR and/or medication prior to countershock, see Menegazzi, J J, et al., "Ventricular Fibrillation scaling exponent can guide timing of defibrillation and other therapies," Circulation, 109(7):926-931, 2004. Those studies have demonstrated that in prolonged VF (that is, ventricular fibrillation in which the ScE has progressed to 1.3 or higher), providing CPR and drugs significantly increases survival. The converse of that observation is that defibrillating prior to other interventions in prolonged VF is detrimental and leads to a decrease in potential survival.

The scaling exponent has a rise in value over the first 5 minutes and then plateaus for a period of 4 minutes before again rising. This makes separation of time periods before and after 5 minutes difficult. A method based on non-liner dynamic methods which provides a measure related to the frequency of the ventricular fibrillation waveform was therefore developed which is termed the "angular velocity" (AV), see Sherman, L D, et al., "Angular velocity: a new method to improve prediction of ventricular fibrillation duration", Resuscitation, 60(1): 79-90, 2004. The angular velocity, (AV), is based on the formation (from 3 'lagged' copies of the time series data of the VF waveform) of a structure in three dimensional phase space which rotates around a central point in a disc shaped region. The velocity of rotation of the leading edge of the position vector which forms this structure over time decreases with the duration of VF. If a 5 second recording of VF is examined with this method, it provides an estimate of the time period at which the VF was obtained.

Although each of the two methods, the scaling exponent and the angular velocity, have limitations individually, they can be combined to increase the sensitivity and specificity of the overall analysis of ventricular fibrillation into episodes less than 5 minutes and episodes greater than 5 minutes. In fact, the combination of these two methods in the laboratory with VF recorded at 1000 samples/sec and without filtering of the signal allows one to predict with 90% sensitivity that the VF being examined is from a subject with VF of less than 5 minutes duration. Specificity with this method is 75%.

The scaling exponent was developed in a laboratory setting in which recording could be done in an optimal manner in order to acquire data sufficient to calculate the scaling exponent and the angular velocity accurately. Specifically, the recording rates were 1000 samples/second and the data were acquired without filtering of any type. Modern cardiac defibrillators, AEDs, and monitoring equipment that is currently in use do not provide for data acquisition at these rates and the signal acquired is highly filtered, usually below 40 hertz, in order to apply computer algorithms which are used to analyze the ECG traces for cardiac rhythm, rate and other features of interest. Typical sampling rates are less than 125 samples per second and the signal is low pass filtered to allow only the part of the signal less than 40 hertz to be acquired. This is not a problem for frequency based measures, such as Fourier analysis or for angular velocity measurements, because the power of frequencies present in ventricular fibrillation are predominantly below 20 hertz. However, studies of filtering and sampling rates do demonstrate that the value of the scaling exponent is severely decreased by filtering and by reducing the sampling rate. This is demonstrated in FIGS. 1 and 2 which show the mean ScE calculated over a period of 13 minutes from VF recorded at 1000 samples/sec without filtering in FIG. 1 and the ScE for the same group of recordings decimated to a rate of 62.5 samples/sec and low pass filtered to below 31.25 hz. In these real world circumstances, the scaling exponent loses almost all of its predictive ability. In contrast, the angular velocity is not severely affected by the recording conditions as present in currently used devices. This is shown in FIG. 6. In order to be able to separate VF of under five minutes from that over 5 minutes and to better predict duration of VF and the probability of successful defibrillation attempts, a method which measures information which is similar to that measured by the scaling exponent but which is not affected by the sampling rates and digital filters present in currently used clinical devices is clearly needed.

While progress has been made in developing methods for determining the duration of ventricular fibrillation and likelihood of successful defibrillation, it remains desirable to develop improved devices and methods for determining the duration of ventricular fibrillation as well as improved treatment devices, methods and protocols for treatment of ventricular fibrillation based on these.

OBJECTS AND ADVANTAGES

Accordingly, several objects and advantages of the present invention are:
(a) to provide a method to measure a characteristic or characteristics of the ventricular fibrillation waveform which is associated with a state or phase of ventricular fibrillation which is based on principles that are distinct from the prior art and therefore may provide information not present in measures represented by the prior art.
(b) to provide a measure of a characteristic or characteristics of the ventricular fibrillation waveform which can be performed on waveform data obtained at sampling rates below 125 samples/second and therefore can be obtained from currently available clinically utilized defibrillators and monitoring devices.
(c) to provide a measure of a characteristic or characteristics of the ventricular fibrillation waveform which can be performed on waveform data which has been filtered with low pass filters that leave only frequencies below 50 hertz and therefore can be obtained from currently available clinically utilized defibrillators and monitoring devices.

Still further objects and advantages will become apparent from a consideration of the ensuing descriptions and drawings.

SUMMARY OF THE INVENTION

In general, the present invention provides a new quantitative measure of the heart rhythm waveform, and particularly, the ventricular fibrillation waveform, related to the autocorrelation of the voltage values of the ECG waveform (for example, the logarithm of the sum of the absolute values of the series of values of the series of values in the autocorrelation function as calculated for the waveform segment). The logarithm of the sum of the absolute values of the series of values of the autocorrelation function, termed the LAC (for Logarithm of the Absolute Correlation), can be calculated from a very short interval of ventricular fibrillation waveform. In studies of the present invention 5 second intervals of waveform were analyzed in less than one second.

As will be described, the LAC is based on calculating the autocorrelation function for a 5 second segment of VF and then taking the absolute value of each value in the series of values forming the autocorrelation function and summing these values. The base 10 logarithm may then be taken and this is used as an estimate of the duration for which ventricular fibrillation has been present and of the likelihood of ventricular fibrillation being successfully terminated by an electrical shock.

In one aspect, the present invention is a method of determining or characterizing a state of the myocardium, in particular it determines or characterizes a state of ventricular fibrillation of the myocardium, including: measuring the rhythm of the heart during ventricular fibrillation for a period of time; creating the autocorrelation function of the series of voltage values for this period of time for this measured heart rhythm; summing the absolute values of each of the series of autocorrelation values in the autocorrelation function; determining a first value related to the sum of the autocorrelations of the voltage values over a period of time; and determining the state of ventricular fibrillation by relating the first value to the state of ventricular fibrillation.

The first value can, for example, be the logarithm to the base 10 (or any other convenient base) of the sum of the absolute values of the autocorrelation function values. The autocorrelation function can be formed by first taking the mean or arithmetic average of all voltage values for the period of time to be considered and subtracting this mean from each voltage value in the series. This results in a series of voltage values that are centered about the mean for the segment of time under consideration. Then the first member of the series of values is multiplied times the second member of the series. The second member is multiplied times the third member, the third member times the fourth member, and so on, until the end of the series of values is reached. These individual products of values separated from each other by 1 value are then summed and form the "autocorrelation at a lag of 1". Then, beginning at the start of the series, the first member is multiplied times the third member, the second member times the fourth member, and so on, until the end of the values are reached. These individual products of values separated by 2 values are again summed. This sum forms the autocorrelation at a lag of 2. This process is repeated at increasing lags for as many lags as is desired, for a 5000 point sample, 500 lags could be used. When the sample has 310 points, 30 or more lags could be used. The series of autocorrelations at each lag from 1 to 500 (or 1 to 30 depending on the particular circumstances) form the autocorrelation function. Each of these values in the autocorrelation function is then made to be positive by taking its absolute value. This series of absolute values of the autocorrelation function is then summed to give a total. The total itself or the logarithm of this total may then be used as first value. The logarithm of the total could be taken to the base 10 or the base 2 or any other convenient base.

The method can further include determining a second value related to the angular velocity of the ventricular fibrillation heart rhythm for a period of time. In this embodiment, the step determining the state of fibrillation includes the step of relating at least one of the first value and the second value to the state of fibrillation. The first value and the second value are preferably both related to the state of fibrillation. The second value can be one of several values related to (and including) the angular velocity. Several different techniques provide estimates of the frequencies which make up the fibrillation waveform. These include but are not limited to the angular velocity and the median frequency measures. The angular velocity has several advantages over the median frequency measure, including not increasing at late time periods. Other measures related to the Fourier analysis of the frequencies in the VF waveform segment may also be used.

As noted above, the ECG waveform output used in calculating the LAC may be filtered and may be obtained at sampling rates which are routinely used in currently available clinical instruments. Filtering and sampling rates present in all devices used clinically at the present time severely affect the values of the scaling exponent and other measures of fractal dimension. However such sampling rates and low pass output filtering does not affect the LAC. In several studies of the present invention, sampling rates of 62.5 samples/second and low pass filtering to eliminate frequencies over 31.25 hertz did not significantly affect the LAC values. This is shown clearly in FIGS. 5 and 6.

In one embodiment, the determined state of the ventricular fibrillation is associated with a probability of success of a mode of treatment of ventricular fibrillation. The mode of treatment can, for example, be a defibrillation shock. The determination of the probability of success of a defibrillation shock can, for example be related to both the LAC and the angular velocity. The measured values (or one or more values derived there from) can, for example, be compared to stored or historical values of the variables or to the output of one or more values derived from such values. Values other than the first value and/or the second value can also be determined. Moreover, the first and/or second values can be measured over multiple periods of time in determining the state of ventricular fibrillation.

In another embodiment, the invention provides a method of determining a treatment for a patient experiencing ventricular fibrillation, including: measuring the rhythm of the heart during ventricular fibrillation for a period of time; calculating the LAC from the voltage values in the measured ventricular fibrillation heart rhythm; determining a first value related to the LAC calculated from the rhythm over the period of time; and relating the first value to a treatment for the patient. As described above, the first value can be the sum of the absolute values of the autocorrelation function values or the logarithm to the base 10 of this same sum. As also described above, the method can further include determining a second value related to the angular velocity of the rate of rotation of the position vector which is the leading edge of the phase space reconstruction about the center of mass of the points of the ventricular fibrillation for the period of time. In that embodiment, the step of determining the treatment can include the step of relating at least one of the first value and the second value to the treatment. Once again, the second value can be the angular velocity or some other measure based on the frequencies present, the frequency spectrum, in the VF waveform segment.

In a further aspect, the present invention provides a system for providing an indication of a state of ventricular fibrillation. The system includes at least one sensor to measure the heart rhythm and at least one processor in communication with the sensor. The processor is adapted to calculate the LAC for a period of time and to determine a first value related to the LAC for the period of time. The system further includes a user interface system in operative connection with the processor. The user interface system is adapted to provide information related to the first value, for example, over multiple periods of time. The processor can be further adapted to determine a second value related to the angular velocity or the frequency spectrum of the ventricular fibrillation for the period of time. In this embodiment the user interface system is adapted to provide information related to at least one of the first value and the second value.

In another aspect, the present invention provides a defibrillation system for use in treatment of ventricular fibrillation. The system includes at least one sensor to measure heart rhythm and at least one applicator to apply a defibrillation pulse to a patient (either human or another member of the animal kingdom). The system further includes at least one processor in communication with the sensor and the applicator. The processor is adapted to calculate the LAC over a period of time and to determine a first value related to this calculation over the period of time. The system further includes a user interface system in operative connection with the processor to provide information related to the LAC to a user. The processor can further be adapted to determine a second value related to the angular velocity or other measure of the frequency spectrum of the ventricular fibrillation waveform for the period of time. In that embodiment, the user interface provides information related to at least one of the first values and the second value.

In another aspect, the present invention provides a method of creating a relation to characterize ventricular fibrillation including: measuring heart rhythm during ventricular fibrillation for an epoch comprising a period of time for a number of unique epochs; calculating the LAC of the measured ventricular fibrillation heart rhythm for each epoch; and determining a first value related to the LAC for each epoch. Preferably, the unique epochs are sequential epochs. The unique epochs can, for example, be sequential epochs of approximately 5 seconds.

In still a further aspect, the present invention provides a method of determining a state of a heart rhythm waveform, including: measuring the rhythm of the heart for a period of time; calculating the LAC for the period of time; determining a first value related to the LAC for the period of time; and determining the state of the heart rhythm waveform by relating the first value to the state of the heart rhythm waveform.

The LAC of the ventricular fibrillation waveform varies in a predictable manner over time during ventricular fibrillation and quickly provides a characterization of the ventricular fibrillation waveform that can be related to a "character", "phase", or "state" of ventricular fibrillation. In that regard, ventricular fibrillation appears to exhibit different states which can be associated with different preferred treatment protocols. Such states of ventricular fibrillation can be related to the duration of ventricular fibrillation as untreated ventricular fibrillation appears to pass through various states throughout its duration. For example, as described above, the likelihood of successful defibrillation is determined, in significant part, by the duration of ventricular fibrillation, and a measure of ventricular fibrillation duration can serve as a way of estimating the likelihood of shock success. For this purpose, shock success can be defined as the restoration of a perfusing or organized cardiac electrical rhythm, or as the suppression of ventricular fibrillation, within a short period of time following the application of the defibrillation shock (usually within approximately a minute). Duration of ventricular fibrillation is not the only determinant of shock success, however. If, for example, cardiopulmonary resuscitation or CPR is applied for a period of time during ventricular fibrillation, the likelihood of shock success can be greater than if the patient did not receive CPR. Moreover, if ventricular fibrillation is triggered by a progressive ischemic event rather than a sudden electrical event, such ventricular fibrillation is more difficult to shock successfully for the same duration of ventricular fibrillation. The inventor has discovered that certain values related to (or a measure of) the LAC, particularly when used in conjunction with a value related to (or a measure of) the rate of change of a phase space reconstruction of the ventricular fibrillation waveform (such as the angular velocity) or other frequency based measures (such as the median frequency) seem to take any and all of the factors affecting the state of ventricular fibrillation into account, allowing, for example, a prediction of shock success to be made without having to consider such individual factors.

The LAC, for example, exhibits a distinct pattern in which there is a linear decrease in value over time from the initiation of ventricular fibrillation until approximately 4 to 5 minutes of duration. The LAC value then remains relatively stable at a plateau until approximately 9 minutes of duration following which it then decreases in a linear manner. This is shown in FIG. 3. In a study of the present invention, when the LAC (which took less than 1 second to calculate) was used in the present invention in conjunction with the angular velocity to establish that less than 5 minutes of ventricular fibrillation had passed, over 90% of waveforms from this period of VF were identified on the basis of a single 5-second recording of the waveform. In addition, when the same analysis was performed on waveform segments from periods of time representing VF of over 5 minutes duration, the negative predictive value was 93%. This is shown in FIG. 13B. The LAC is not altered by recording conditions present in currently used clinical practice, for example, digital recording of the waveform at a rate of less than 62.5 samples/second and filtering of the ventricular fibrillation waveform by low pass filters which restrict the signal to less than 31.25 hertz frequencies do not alter the values of the LAC. The sensitivity and negative predictive value cited above were in VF recorded at 62.5 samples/sec and low pass filtered to below 31.25 hertz. As the appropriate treatment of ventricular fibrillation is strongly dependent upon the state of ventricular fibrillation (which, in turn, is often related to the duration thereof), and as the devices in current clinical use provide for waveform recordings which are limited to lower sampling rates and are filtered to eliminate higher frequencies, the improved devices and methods of the present invention, which provide an indication of the state of ventricular fibrillation from a short segment of heart rhythm recorded with lower sampling rates and with filters that eliminate higher frequencies, provide a significant improvement in the art.

BRIEF DESCRIPTION OF THE DRAWINGS

Other aspects of the invention and their advantages will be discerned from the following detailed description when read in connection with the accompanying drawings, in which:

FIG. 3 illustrates the mean value of the LAC in 45 recordings performed in the laboratory at 1000 samples/sec with no filtering.

FIG. 4 illustrates the mean value of the "LACadjusted" (as described in the text) compared to the mean value of the ScE as calculated from 45 recordings performed in the laboratory at 1000 samples/sec with no filtering.

FIG. 5 illustrates the lack of affect of reducing sampling rates to 62.5 samples/sec and applying low pass filtering below 31.25 Hz (ranges consistent with current clinically used devices) on the mean value of the "LACadjusted".

FIG. 6 illustrates the mean value of the AV in 45 recordings performed in the laboratory at 1000 samples/sec with no filtering and the mean AV of the same group of recordings after decimation to 62.5 samples/sec and low pass filtering below 31.25 Hz.

FIG. 11 illustrates the placement of the "classification line" used to separate the two groups of ventricular fibrillation (under 5 minutes and over 5 minutes) for the analysis of sensitivity and specificity in the 2×2 tables, here performed on a plot LACadjusted versus AV probability density in laboratory data.

FIG. 12 illustrates an embodiment of the present invention consisting of an automated external defibrillator with display which incorporates a protocol or tool to determine the duration of ventricular fibrillation or the likelihood of success of a defibrillation shock.

FIG. 13A shows the 2×2 table for the LACadjusted versus AV analysis in recordings at 1000 samples/sec and no filtering.

FIG. 13B shows the 2×2 table for the LACadjusted versus AV analysis in recordings at 62.5 samples/sec and low pass filtering below 31.24 Hz.

FIG. 14A shows the 2×2 table for the ScE versus AV analysis in recordings at 1000 samples/sec and no filtering.

FIG. 14B shows the 2×2 table for the ScE versus AV analysis in recordings at 62.5 samples/sec and low pass filtering below 31.25 Hz.

DETAILED DESCRIPTION OF THE INVENTION

Figure 1:
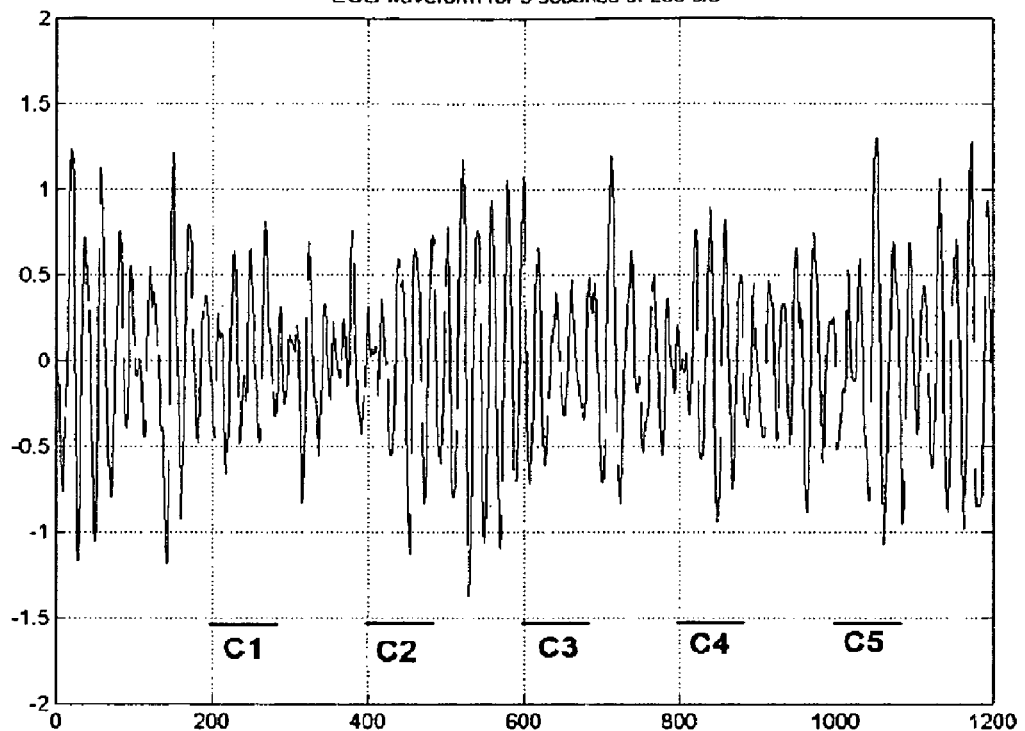
FIG. 1 illustrates the mean value of the ScE in 45 recordings performed in the laboratory at 1000 samples/sec with no filtering.

In studies of the present invention, the ability of the LAC (alone or in combination with the angular velocity) to predict or determine a state, phase or class of ventricular fibrillation as modeled by the duration of ventricular fibrillation was determined. It was compared to the scaling exponent which appears to measure some of the same underlying characteristics of the ventricular fibrillation waveform, but which requires recording conditions which are not present in monitors and defibrillators in current use. Specifically, the scaling exponent does not produce useful results at sampling rates below 125/second or with filtering below 60 hertz. The LAC is unaffected at these sampling rates and low pass filtering conditions.

In a study of the present invention, a classification system including two classes of ventricular fibrillation were used. In the first class of less than 5 minutes duration, defibrillation is likely to be successful and in the second class of over 5 minutes duration, defibrillation is not likely to be successful. As described above, a delineation based upon a ventricular fibrillation duration of 5 minutes has been related to the success of a defibrillation shock and to survival. Although the methods and devices of the present invention are discussed herein generally in terms of a classification system including two classes, a classification system having greater than two classes or a continuous classification system is readily set forth.

In several studies of the present invention, using recordings up to 12.5 minutes of ventricular fibrillation from 45 healthy swine which were obtained prior to any interventions, the angular velocity method, scaling exponent method and the LAC method were used to create sets of two-dimensional scatter plots as described below. Probability density estimates based on these scatter plots were then used to establish objective criteria for separating ventricular fibrillation of less than 5 minutes duration from ventricular fibrillation of over 5 minutes duration. This process was performed in data initially recorded at 1000 samples/second without filtering. It was then repeated on data decimated to a recording rate of 62.5 samples/second and then filtered to 31.25 hertz with low pass filters.

In the studies of the present invention, (which were approved by the University of Pittsburgh Institutional Animal Care and Use Committee), seventy-two mixed-bred domestic swine of either sex were sedated with intramuscular ketamine (10 mg/kg) and xylazine (4 mg/kg) and then anesthetized with intravenous alpha-chloralose (40 mg/kg bolus followed by 10 mg/kg/hr drip). The swine were intubated with a 5.0 cuffed tracheal tube and ventilated with room air at a tidal volume of 15-20 cm3/kg and a rate of 12-16 respirations/min. Eucapnia was assured and adjusted to between 35 and 45 mmHg by using end-tidal side stream carbon dioxide monitoring from a LifePak 12 monitor defibrillator (available from Medtronic Physio-Control Inc. of Redmond, Wash.). Neuromuscular paralysis was achieved with pancuronium (4 mg IV bolus, repeated 2 mg IV bolus as needed), and right femoral arterial and central venous catheters were placed in the descending aorta and right atrium with micro-manometer tipped pressure transducers for continuous recording. The electrocardiogram and arterial pressure tracings were continuously digitally recorded at a rate of 1000 points/sec using the Chart software package (version 3.6, available from AD Instruments of Castle Hill, Australia). Ventricular fibrillation was induced by a transthoracic 3 second, 60 Hz, 100 mA AC current.

The VF waveform obtained for analysis was then recorded from the animal as unfiltered lead-II signal via a wide bandpass preamplifier (Model DAM 50, available from World Precision Instruments of Sarasota, Fla.) with a 10-fold dc gain. The unfiltered signal was then sent through an SCC AI07 signal conditioning unit available from National Instruments in an SCC 2345 chassis (National Instruments), where it was amplified 200-fold and passed directly to a PC 6024E NI-DAQ data acquisition card (National Instruments). The leading edge of the trajectory in phase space was traced out using a DELL® PENTIUM® 3 based computer. The signal was acquired at a rate of 1000 Hz in a double buffer of 10,000 points so that a 5000-point sample was taken into the buffer every 5 seconds. Using C++ code (Microsoft Visual C++ 6.0), the ScE was calculated, displayed and recorded in real time at 5 seconds intervals.

In all, 72 animals were involved in a protocol. The animals were placed in VF, which was allowed to continue until the animals reached ScE values (calculated in real time) of 1.1, 1.2, 1.3 or 1.4, before one of several interventions were applied and attempts at resuscitation were begun. The animal study protocol used in the studies of the present invention is described in detail in Menegazzi, J J, et al., "Ventricular Fibrillation scaling exponent can guide timing of defibrillation and other therapies," Circulation, 109(7):926-931, 2004. A total of 45 swine were allowed to reach an ScE of 1.3 or 1.4. Swine in which the ScE was allowed to reach only 1.1 or 1.2 were in VF for less than 5 minutes and were not in VF for a sufficient length of time to be included in the study of VF duration of the present invention. Many of these recordings were of less than 60 seconds duration to reach an ScE of 1.1 and less than 3 minutes to reach an ScE of 1.2. No other inclusion or exclusion criteria were used. For statistical purposes there were a sufficient number of animals in whose case VF was recorded to 12.5 min or greater to allow analysis to the 12.5 min time period. The 45 recordings were then decimated by a factor of 16 using the MATLAB (Release 12, version 6.0.0.88, 2000, available from Mathworks, Inc.) standard decimation function "decimate( . . . )" resulting in a sampling rate of 62.5 points/second. The 45 recordings were then filtered with MATLAB using the "ellip" filtering function to obtain the filter coefficients and the function "filter( . . . )" to apply these coefficients to the waveform. The result was to obtain the final filtered waveform of each of the 45 recordings with low pass filtering below 31.25 Hz at a sampling rate of 62.5 samples/sec.

The recordings of unfiltered and then decimated/filtered data were analyzed for both the changes in logarithm of the sum of the absolute values of the autocorrelation function over time (referred to as the "LAC"), the scaling exponent over time (referred to as the "ScE") and the phase space reconstruction with calculation of the rotational velocity of the position vector over time (referred to as the "AV"). These values were then analyzed as described below.

LAC:

The consideration of correlations, in a manner similar to my previous work with the angular velocity, began with considering the VF waveform as being possibly derived from a "Chaos" type mechanism related to nonlinear dynamics. One important idea of chaos theory is that of the "correlation" or "autocorrelation" of a time series, see for instance, G P Williams; "Chaos Theory Tamed, 101-105; Joseph Henry Press, Washington, D.C., 1997. The general method for obtaining the "autocorrelation function" is described therein.

To form this particular numerical statistic, the LAC, one first records the period of VF from which the LAC will be calculated. In this experiment sequential segments of VF from each of the 45 recordings were analyzed. These segments were recordings of 5 seconds of VF. If the sample was recorded at 1000 samples/second, this was 5000 points. For a segment of VF waveform recorded at 62.5 samples/sec this was approximated with 310 points. The segment of VF was then "centered" about zero by taking the sum of the 5000 (310 if recorded at 62.5 samples/sec) voltage values and dividing by 5000 (310 if recorded at 62.5 samples/sec). This gave the average or mean. The mean was then subtracted from each voltage value in the recording so that the series was centered about zero. It is to be understood that in all calculations of the autocorrelation function the data were first centered in this manner prior to the calculations. It is also possible to perform the calculations without centering and this is understood to be another possible variation of the method. Then the following calculations were performed on this centered data set. This example is for 5000 point data sets. It was also performed on 310 point data sets when used to analyze recordings at 62.5 samples/second which were filtered to less than 31.25 hertz. It is clear that other sample sizes could also be employed.

The autocorrelation was formed as follows: a data series "y" of 5000 points can have each of its members identified as $y[0], y[1], y[2], y[3] \ldots y[4999]$. A specific value would be $y[k]$ where k is one of the numbers between 0 and 4999. The autocorrelation calculation is done at a succession of 'lags' from 1 to 500 (or in the 300 point data set this could be to a lag of 30 or 60 or other selected maximum lag).

The calculation is as follows:

$$\text{autocorrelation(lag)} = y[\text{lag}+0]*y[0] + y[\text{lag}+1]*y[1] + y[\text{lag}+2]*y[2] \ldots + y[\text{lag}+(4999-\text{lag})]*y[4999-\text{lag}]$$

For instance, for a lag of 1 it is calculated as:

$$\text{autocorrelation}(1)=y[1+0]*y[0]+y[1+1]*y[1]+y[1+2]*y[2]\ldots+y[1+4999-1]*y[4999\text{-lag}]$$

or, after adding the numbers in brackets, $$\text{autocorrelation}(1)=y[1]*y[0]+y[2]*y[1]+y[3]*y[2]\ldots+y[4999]*y[4998]$$

and for lag of 2 it is:

$$\text{autocorrelation}(2)=y[2+0]*y[0]+y[2+1]*y[1]+y[2+2]*y[2]\ldots+y[2+4999-2]*y[4999-2]$$

again, after summing the quantities in brackets, $$\text{autocorrelation}(2)=y[2]*y[0]+y[3]*y[1]+y[4]*y[2]\ldots+y[4999]*y[4997]$$

and this proceeds in like manner up to lag 500.
The final autocorrelation at lag 500 is then:

$$\text{autocorrelation}(500)=y[500]*y[0]+y[501]*y[1]+y[502]*y[2]\ldots+y[4999]*y[4499]$$

The creation of autocorrelations at each lag produces a series of these summations from 1 to 500 which are the:

"autocorrelation(1),autocorrelation(2) . . . autocorrelation (500)."

The "autocorrelation (0)" was not included in calculations here. The inclusion of this first term in calculations could be done and is envisioned as one of the variations of the method. In addition, it should be understood that the number of 'lags' used may be varied by one skilled in the art and represents another variation in the method which is envisioned. The entire series or set of 500 values is called the "autocorrelation function". Each of the members of this series of 500 represents the 'power' of the autocorrelation at that particular lag value. The larger the autocorrelation the higher the degree of association or similarity between the two copies of the waveform which are offset by the lag. If a particular sum of values forming a member autocorrelation function series is negative (as will occur if many of the values are on opposite sides of zero. For instance if one of the values, say "y[200]" is positive, and the other value, for instance "y[200+lag]", is negative), a negative product results. If many of these are related in this manner at a particular lag, then the sum will be negative. This represents a negative or "anti-correlation" which, in a sense, also represents power or similarity. It represents the ability to predict that the there is a high likelihood that the two waves ( i.e. the original wave and the offset or lagged wave) will have many corresponding points in opposite directions from the mean of zero. They are 'negatively' correlated. This is also, therefore, a measure of predictability. Of importance here is the predictive power that is present, whether of the positive or negative type. In order to properly measure the total power, that is the sum of both the positive and the negative "power" of the autocorrelation, the absolute value of the autocorrelation is used. This prevents positive and negative members of the autocorrelation function from "canceling each other out". Another method would be to use the squares of the members of the autocorrelation function series to produce a positive result. The method of using absolute values will be described herein. One skilled in the art could easily use the squares to produce a positive representation of the power, or could take absolute values prior to forming the products, or use equivalent methods.

Therefore, the next step was to make each of the 500 autocorrelations positive by taking the absolute value. Then all 500 of the positive values of autocorrelation in the autocorrelation function were summed. This total can be used as it is. However, it was deemed here to be more useful to take the logarithm of this total using the base 10. This makes plotting and comparisons easier to follow and was therefore the summary measure chosen to represent the value calculated. As noted above, the logarithm could also be taken to bases other than 10. This value was then used to estimate the approximate time period of VF and to estimate the likelihood of successful defibrillation. One skilled in the art could use the statistic without taking the logarithm at this point, or could use other bases.

The code in the C+ programming language for a function to perform this calculation on a time series of 5000 points of VF waveform is as follows: The ventricular fibrillation waveform is read in as a sample of 5000 points called 'VF':

```
for(i=0;i<4999;i++)
{
y[i]=VF->data[i];     //THIS READS IN THE y[i] from the "VF" data series
ytot=y[i]+ytot;       //this is the SUM OF y[i]
}
reads in the values of y from 0 to 4999.
```

The function to calculate the LAC is as follows:

```
double Correl_sum(vfwaveform_ptr VF)
{
long int
long flag, i,j,k,m,r,u,v;int pointnumber ;
double input;
double y[60000]={0,0,0};
double autoco[500]={0,0,0};
int totnumber[1000]={0,0,0};
double ytot;
double ymean;
double autocotot;
double abstot;
double logabstot;
double y1y1;
int kk;
int klagmax;
int voltcount;
klagmax=500;
pointnumber = 0;
ytot=0.0;
ymean=0.0;
autocotot=0.0;
i=0; j=0; k=0; y1y1=1.0;
for(i=0;i<4999;i++)
{
y[i]=VF->data[i];     //This reads in the VF waveform to the y[i] series
ytot=y[i]+ytot;       //this is the SUM OF y[i]
}
pointnumber = i;
ymean=ytot/pointnumber;
for(k=0;k<=4999;k++)
{
y[k]=y[k]-ymean;      //THIS IS THE MEAN CALCULATION TO
                      //CENTER THE WAVEFORM AROUND 0.0
}
for ( k=1; k<=klagmax; k++ )
{
for ( r=0; r<=pointnumber-1-k; r++ )
{
autocotot=autocotot+((y[r+k])*(y[r])); //THIS IS y(t)*y(t+k) added to a total
}
//THE NEXT LINE PROVIDES THE ABSOLUTE VALUE OF
//EACH VALUE IN THE AUTOCORRELATION FUNCTION
autoco[k]=fabs((autocotot/((double)(pointnumber-2-k)))*5000.0);
```

-continued

```
//THIS ALSO IS CODE TO TAKE THE SUM FOR 5000-K VALUES
AND)
//MAKE IT GOOD FOR 5000 VALUES
autocotot=0.0;
}
abstot=0.0;
for(j=1;j<=500;j++)
{
abstot=abstot + autoco[j];
}
logabstot=log10(abstot);
return logabstot;    // THIS IS THE LAC VALUE
}
//END OF CODE FOR LAC
```

This therefore demonstrates the essentials of the method and could be used by anyone skilled in the art to recreate the method and to calculate the LAC and make the device capable of performing and utilizing this calculation.

As conceptualized, the LAC is a measure of the order in the data series. The method above was used to calculate the LAC for each recording in the series of 45 as noted above. These calculations were performed on recordings of VF waveform obtained at 1000 samples/second and no filtering and then repeated on the same waveform decimated as described above to 62.5 samples/second and low pass filtered to 31.25 Hz. The LAC values were adjusted using the following mathematical transformation to allow easier direct comparison to the scaling exponent. The "LACadjusted"=(1.39-(LAC/6.55)). This conversion or transformation merely places the LAC values in increasing order at approximately the same range of values as the scaling exponent. It is included here to facilitate comparison and understanding of this method when compared with prior methods. It is noted that the LAC and the scaling exponent measure and quantify a similar characteristic or quality of the waveform, i.e. the feature related to amplitude and/or scale. The LAC does not utilize the prior art in any manner to achieve this measurement and is in no way derived from this prior art.

Scaling Exponent:

As described above, the scaling exponent is a measure of the "roughness" of the VF waveform. It was derived from the fractal self-similarity dimension and its evaluation here is based on the method of Higuchi for time series data. See Higuchi, T., "Approach to an irregular time series on the basis of the fractal theory," Physica D, 31:277-83, 1988. The determination of the scaling exponent is described in detail in Callaway, C W, et al., "Scaling structure of electrocardiographic waveform during prolonged ventricular fibrillation in swine," Pacing Clin Electrophysiol, 2:180-91, 2000; Sherman, L D, et al., "Ventricular fibrillation exhibits dynamical properties and self-similarity," Resuscitation, 47(2): 163-73, 2000 and U.S. Pat. No. 6,438,419, the disclosures of which are incorporated herein by reference.

Given a data set of length n, the sum of potential changes, L, of the segment was calculated for different sampling lags, k. The points are denoted by $Y_i$, which is the ith measurement in the series. The sampling lag, k, was varied from 1 to 40. For each sampling lag, the distance or average difference separating the (i)th and (i+k)th points measured in the interval was calculated as $$<l(k)> = (1/(n-k))\left(\sum_{i=1 \text{ to } n-k} |Y_i - Y_{i+k}|\right).$$

Here the symbol < > indicates the average value of l for a total of (n-k) measurements, using a separation of k units between points. The total potential difference for the entire data set at the lag of k, i.e. L(k), was then calculated as: L(k)=<l(k)>·(n/k). The L(k) thus calculated for the series at k values from 1 to 40 were then fitted to the exponential function:

$$L(k)=k^{(1-d)}.$$

Taking the logarithms of this equation yields log L(k)=(1-d) log k. By plotting "log L(k)" versus "log k" a curve is produced. If there is a linear portion, the slope of this line is (1-d). When there is "scaling" behavior a linear segment or plateau will be identified. In the analysis of VF waveforms all curves should show a clear region of scaling, with a definite plateau. This was observed in VF when recorded at 1000 samples/sec and unfiltered. This plateau was identified using 10 points centered on the inflection point of the curve occurring between k=2 and k=40. The value of d was determined at this point from the slope of the line fitted by least-squares linear regression to a plot of log L(k) versus log k, such that d=1-slope. When analyzing recordings decimated to a recording rate of 62.5 samples/sec and low pass filtered to below 31.25 Hz, there was no true plateau. Instead the first 3 points were used to calculate a slope. This utilized the first and flattest portion of the curve formed to function as the "plateau" for estimation of the slope required to calculate the ScE. Conceptually, the ScE is a summary statistic which reflects how estimates of the total length L(k) varies with the sampling lag k. Lower values of ScE correspond to VF which appears "coarse" to the clinical observer, and higher values correspond to VF which appears "fine".

Figure 2:
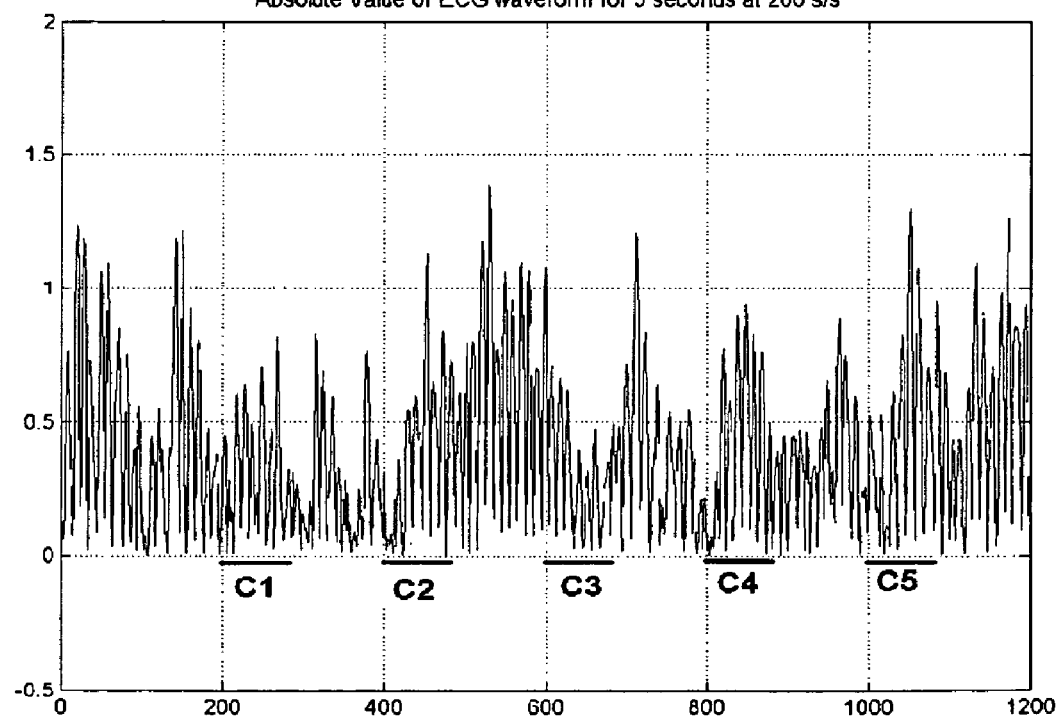
FIG. 2 illustrates the affect of reducing sampling rates to 62.5 samples/sec and applying low pass filtering below 31.25 Hz (ranges consistent with current clinically used devices) on the mean value of the ScE.

Calculations of the ScE were performed on the original unfiltered data recorded at 1000 samples/second and on the data decimated to 62.5 samples/second and low pass filtered below 31.25 hertz. Results of scaling exponents calculated for 45 unfiltered recordings at 1000 samples/second over the 12.5 minute duration of VF are shown in FIG. 1. There was an increase in the ScE over the full interval. In the initial 5 minutes of VF, there was a rapid rise in the ScE. However, the middle portion of the ScE plot formed a plateau for approximately 3 minutes, from 5 to 8 minutes. After 8 minutes, the ScE increased through the remainder of the 12.5 minutes of VF duration. The standard deviation at each point was noted to be comparatively large after the first 4 minutes and in the plateau of the curve from 5 to 8 minutes. Thus, separation of time periods was difficult over that range of time. The initial rapid increase at times less than 5 minutes made the early portion of the curve useful when combined with the AV in a two-dimensional probability density analysis as described below. The results for the same analysis performed on the data decimated to 62.5 samples/second and low pass filtered to less than 31.25 hertz are shown in FIG. 2. Here the ScE values are completely different from the original values and, in fact, the general trend of ScE values are reversed with a decrease in the ScE as duration of VF increases up until about 10 minutes with an increase thereafter. This represents a complete loss of the fractal dimension information and a disruption of the method and is an artifact of attempting to apply the method in conditions for which it is not suited, i.e. in situations in which a true plateau is not present.

The LAC and the ScE can be compared directly over the time course from initiation of VF until approximately 12.5 minutes. A close examination of the two plots shows that the ScE (FIG. 1) and the LAC (FIG. 3) have very similar, although opposite patterns. The ScE rises to between 4 and 5 minutes and then plateaus until 9 minutes and then rises. The LAC clearly follows the opposite pattern. Investigation of these patterns led to the development of a conversion of LAC values to values that approximate the ScE. This is done to allow comparison. It is felt that the qualities or characteristics of VF measured by the two measures are similar, although the two methods are clearly distinct and separate. The comparison was done by means of the following formula: The "LAC-adjusted"=(1.39-(LAC/6.55)). By making this adjustment, the LAC and ScE can be directly compared in the original data recorded at 1000 samples/sec. (FIG. 4) and in the data decimated to 62.5 samples/sec and low pass filtered to below 31.25 hz (FIG. 5). This comparison demonstrates that the LAC is unaffected by filtering, whereas the ScE suffers a complete loss of information regarding the fractal dimension which it estimates. In fact, the values of the ScE now follow a reversed pattern in which they decrease with time up until 10 minutes rather than increase. The LAC does not change significantly despite the severe alteration in recording conditions present in the decimated and filtered sample. These conditions are similar to those present in currently utilized clinical defibrillators and monitors. In order for these techniques to be applied using currently available devices it is essential that methods be available which allow them to be adapted for the analysis of the VF waveform as described above. It is for this reason that the LAC is a substantial improvement in the state of the art.

Angular Velocity:

The leading edge of the circular structure produced in the phase space reconstruction rotates about the center of mass of the points at an average rate over a 5 second interval. Computer programs written in C++ were used to calculate the average angular velocity of the leading edge of the trajectory over 5 second intervals taken consecutively during the course of VF. The trajectory was formed in the three-dimensional phase space by taking voltage measurements at a sampling rate of 1000/sec, for a total of 5000 points. Indexing the voltages for each interval as Yi, with $1 \leq i \leq 5000$, the points of the trajectory, (x, y, z), can be written as $A_i=(Y_i, Y_{i+k}, Y_{i+2k})$, with i ranging over all points such that $i+2k \leq 5000$, where k is the given lag. The trajectory was then centered about the origin by subtracting the mean of the points from each point. Each point $A_i$ is then treated as a vector based at the origin.

As noted above, the trajectory is planar in three-dimensional phase space. However, the plane of the trajectory changes gradually over the time course of VF. Therefore, the plane was determined for each 5 second phase space reconstruction. The normal vector to the plane was calculated by taking the vector cross product of all temporally consecutive points in the trajectory, and then averaging. That is, the plane normal $N=A_i \times A_{i+1}$ was averaged over all points in the trajectory. Positive rotation was defined as a counterclockwise progression about N (based on a positive cross product using the "right-hand rule"). The angular velocity of the trajectory was then calculated about the N vector, placed at the origin. The measure was defined as the average angular separation between consecutive points in the trajectory in relation to the plane normal, and it carries units of radians per point. At the 1000 points/second sampling rate, this is equivalent to radians per millisecond. The AV is then multiplied by $10^3$ and reported in radians per second. For all points $A_i$ and $A_{i+1}$, and a plane normal N, the separation angle between $A_i$ and $A_{i+1}$ was calculated as $$\theta = \cos^{-1}\left(\frac{A_i A_{i+1}}{|A_i||A_{i+1}|}\right).$$

Since the direction of rotation of the angular velocity was arbitrarily determined by whether the lagged vectors are formed as $(Y_i, Y_{i+k}, Y_{i+2k})$ or $(Y_i, Y_{i-k}, Y_{i-2k})$ it was determined that the absolute value of the angular velocity would be used, regardless of the direction of rotation. The rotation is clockwise or negative in all cases using the convention of $(Y_i, Y_{i+k}, Y_{i+2k})$.

Time series measurements were collected from 45 swine as described above from the initiation of VF to the first intervention. Initial evaluation involved reconstructing the trajectory in three dimensions with 5 second intervals of data. A lag of 10 was therefore chosen for all AV determinations when a recording rate of 1000 samples/sec was used and a lag of 1 was used when the data was decimated to 62.5 samples/sec. Results of angular velocity calculated for 45 swine, for both the original waveform obtained at 1000 samples/second and unfiltered and the decimated recordings at 62.5 samples/second and low pass filtered below 31.25 hertz are shown in FIG. 6. As illustrated in FIG. 6, there was a clear overall decrease in average angular velocity over 12.5 minutes of VF. From 60 seconds of VF there was a gradual increase in the angular velocity from 58 rad/sec until 4 minutes, when it reached a value of 79 rad/sec. From this point forward in time, the angular velocity decreased steadily to 32 rad/sec at 12.5 minutes. The curve was thus multiphasic. It is noted that the AV calculations do not change significantly between the original data and the decimated and filtered data when analyzed. There is a minimal decrease in the peak AV at 4 minutes. The AV rises to 65 instead of to 79. Overall, the AV can be regarded as relatively stable in the range of recording conditions present in currently utilized monitors and defibrillators.

Probability density estimates:

Computer software programs written in C++ were used to estimate the probability density for two dimensional scatter plots of the data. These were performed for the two dimensional combinations of LAC versus AV and also for ScE versus AV. This procedure was performed initially on unfiltered data recorded at 1000 samples/sec. and was then repeated on data decimated to 62.5 samples/sec. and low pass filtered below 31.25 Hz. The analysis was carried out on two separate groups of data. Firstly, all combinations from VF less than 5 minutes were analyzed. Secondly, this procedure was then repeated for all values from epochs of VF from 5 to 12.5 minutes. Probability density estimates were based on the kernel density estimator technique. See Williams, GP, Chaos Theory Tamed, Washington, D.C.: Joseph Henry Press; p. 74-5, 1997, the disclosure of which is incorporated herein by reference. For each recording of VF, the LAC, ScE and AV were each calculated on VF recorded at 1000 samples/second without filtering from the onset of VF to the first intervention performed. All LAC values were converted to "adjusted LAC" values described above to facilitate comparison of the methods. Each calculation was performed on 5000 samples, or 5 seconds of recorded data, and these were done on consecutive epochs until the end of the recording for each animal. For a full 12.5 minutes of recording there would be a total of 150 5-second epochs of data. These calculations were performed for all 45 recordings. Each epoch was regarded as a data point and had individual LAC, ScE and AV values associated with it. By plotting the points in two dimensions, with the LAC or ScE along the abscissa and the AV along the ordinate, a two-dimensional "scattergram" of the points was formed. These two groups of points were then placed on the two-dimensional plots. One plot was of the LAC versus AV and another plot was of the ScE versus the AV. A tent map kernel was then employed (as described in the above reference) using a bin width of 0.02, and density estimates were performed at intersections of a lattice grid from 1.02 to 1.62, with a spacing of 0.02 on the abscissa for LAC or ScE, and from 0.05 to 1.30, with a spacing of 0.05 on the ordinate for AV. At the time of calculation the AV (in the range of 0.040 to 0.120) was augmented by multiplying each value by 10 in order to achieve the same relative range for the LAC or ScE and to allow approximately equal estimates of probability down each axis of the grid based on the utilized bin radius of 0.02. At each point in the lattice all points in the sample were tested to see if they would fall within the bin radius. If the point was within the radius it was weighted according to its distance from the lattice point according to the tent map kernel formula: (1−distance from lattice point/radius). The weighted values of all points falling within the radius were summed and then the sum was divided by the total number of points in the sample and again by the radius to give the probability density estimate at that lattice point. This calculation was done for each of the 744 lattice points. The resulting two-dimensional probability density estimate was then plotted on a surface/mesh plot in MATLAB. Taking all points under 5 minutes and calculating the probability density distribution produced a characteristic picture of the probability that the points in this time range would fall in a particular region of the two-dimensional plot. This procedure was then repeated for all points from 5 to 12.5 minutes and again plotted with a mesh plot on the same three dimensional plot. This process was performed for unfiltered data at 1000 samples/sec and then repeated on the filtered data decimated to 62.5 samples/sec. In the filtered decimated data, epochs of 310 points were used.

Figure 7:
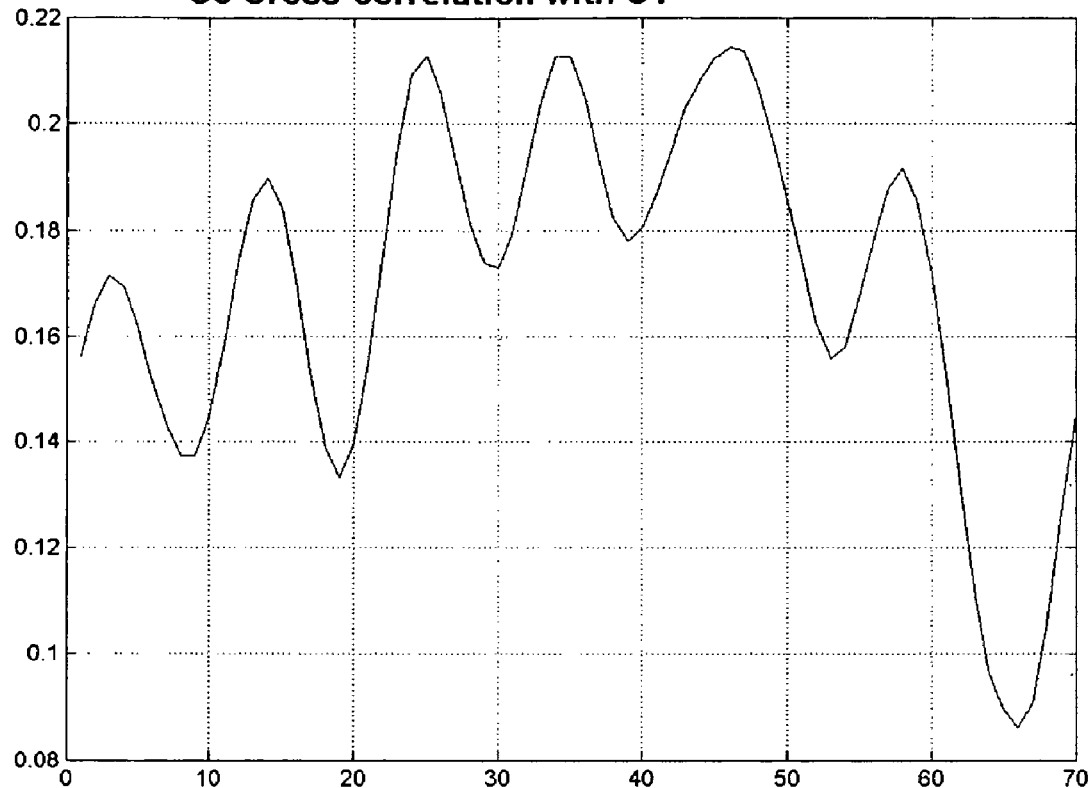
FIG. 7 illustrates a plot of the probability density estimates performed on recordings obtained at 1000 samples/sec without filters for the LACadjusted versus AV values for all epochs of less than 5 minutes of VF compared to the LACadjusted versus AV values for all epochs of VF that were over 5 minutes.

The surface plots of the two groups of VF is illustrated in FIG. 7 for AV and LAC in unfiltered data recorded at 1000 samples/sec and exhibited a higher peak in the less than 5 minute group as a result of the concentration of these values centered around the LAC of 1.10 and an AV of 80 rad/sec values. The group of points greater than 5 minutes exhibited a lower peak at an LAC of 1.27 and an AV of 40 rad/sec. When these two plots were combined, there was a relative minimum (valley) between the two peaks which represented the line where the probability of the points being from one group or the other is equal. This was taken as an initial estimate of the classification line for separating the two classes of points. This is shown in FIG. 11. This line was then approximated using a 7th-degree polynomial using the polyfit function of MATLAB. The "valley" between the peaks followed a line which was increasing initially in the direction of both LAC and AV, although it follows a course with several curves. The final placement of the classification line was then adjusted up or down empirically in order to produce a sensitivity of 90%. This is felt to be a sensitivity which would provide adequate detection of those patients who would benefit from immediate shock treatment of VF. It is understood that other values, (95%, for example), could be utilized in other embodiments of the device.

To determine how effective this classification line was at discriminating between the two groups, all points in the 0-5 minute group were tested with custom software programs developed in MATLAB to determine how many fell outside of the 0-5 min region set off by the classification line. The LAC was calculated for each epoch and the value of the classification line at that LAC was then calculated. If the AV value for that point was greater than the value of the classification line, it was in the "less than 5 minutes duration" VF group, otherwise it was a misclassification. The 5-12.5 minute group was similarly tested for misclassification. By considering the less than 5 min duration VF group as the group with the "disease process" under consideration, a 2×2 table was developed to summarize the sensitivity, specificity, positive predictive value and negative predictive values of the test.

The presence of ventricular fibrillation of a duration less than 5 minutes was taken as the "disease" to be identified by the test. The results for the LAC versus AV calculations are shown in FIG. 13A. The analysis of the LAC and AV calculations for unfiltered data recorded at 1000 samples/sec demonstrated a sensitivity of 90% and a negative predictive value of 92%. This means that if the test value was ventricular fibrillation of greater than 5 minutes, then there is a high probability (92%) that the time frame from which it is taken is actually over 5 minutes. Specificity is also noted to be 69% in this group.

This process was then repeated on unfiltered data at 1000 samples/sec for the ScE showing the previously achieved sensitivity of 90% and a specificity of 75%. This is shown in FIG. 14A.

Figure 8:
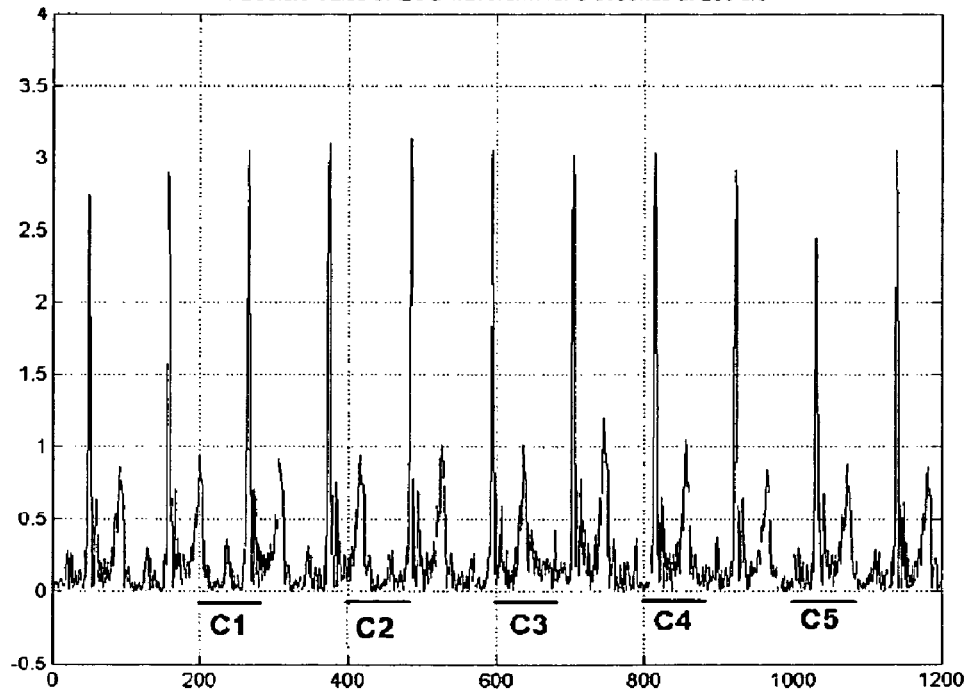
FIG. 8 illustrates a plot of the probability density estimates performed on recordings obtained at 62.5 samples/sec with filtering below 31.25 Hz for the LACadjusted versus AV values for all epochs of less than 5 minutes of VF compared to the LACadjusted versus AV values for all epochs of VF that were over 5 minutes.
Figure 9:
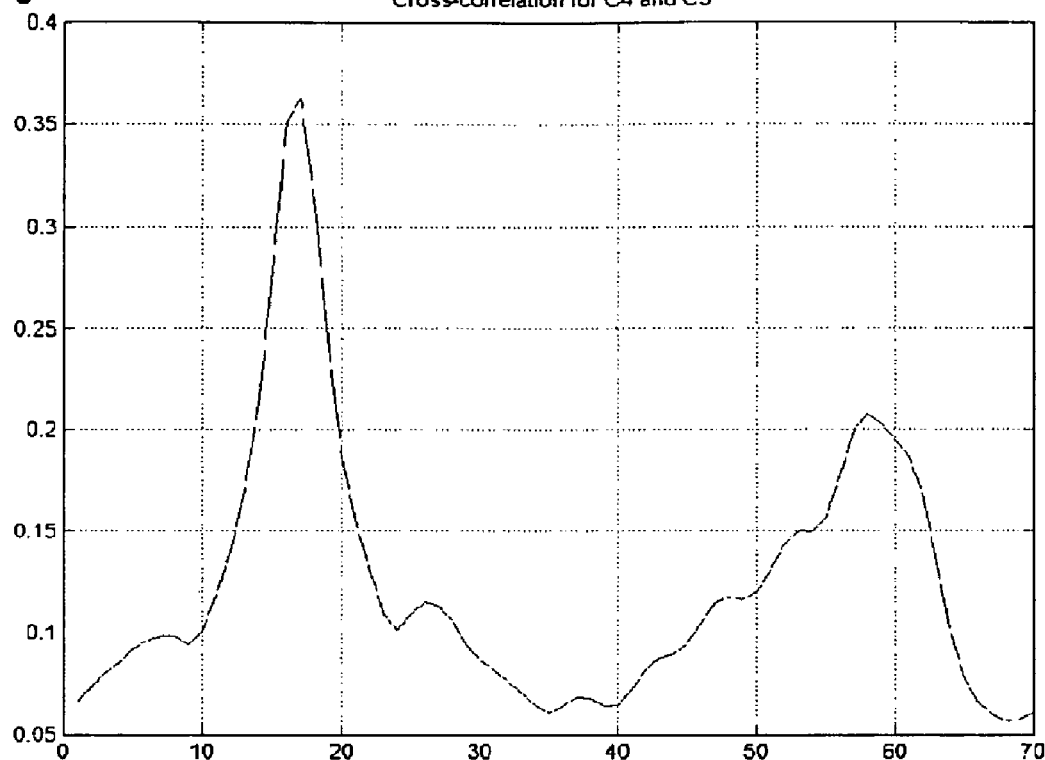
FIG. 9 illustrates a plot of the probability density estimates performed on recordings obtained at 1000 samples/sec without filters for the ScE versus AV values for all epochs of less than 5 minutes of VF compared to ScE versus AV values for all epochs of VF that were over 5 minutes.
Figure 10:
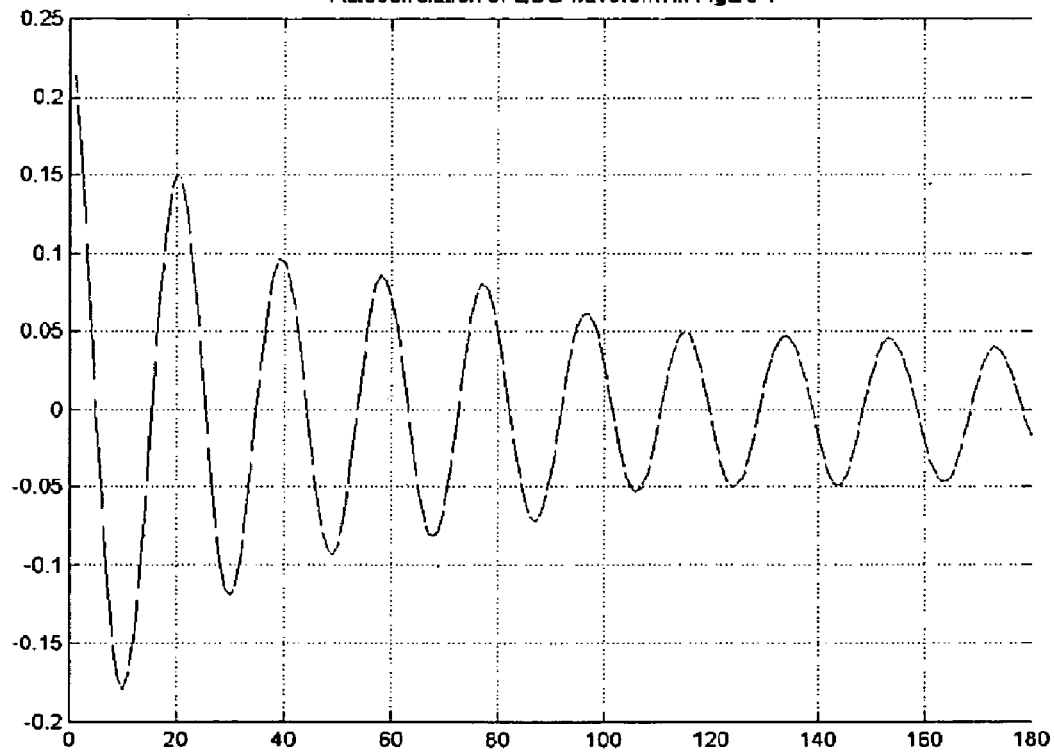
FIG. 10 illustrates a plot of the probability density estimates performed on recordings obtained at 62.5 samples/sec with filtering below 31.25 Hz for the ScE versus AV values for all epochs of less than 5 minutes of VF compared to the ScE versus AV values for all epochs of VF that were over 5 minutes.

This analysis was then repeated for the decimated data at 62.5 samples/sec and low pass filtered below 31.25 samples per second. The results of FIG. 13B were produced for the LAC and AV and the results of FIG. 14B for the ScE and AV. In these figures the sensitivity is again set at 90% with the classification line and the specificity is seen to improve to 75% for the LAC, but to decline to 64% for the ScE. This demonstrates the primary advantage of the LAC over the prior art. In fact, a detailed analysis of the ScE as shown above clearly indicates that its ability to have any predictive power in this regard is actually an unintended accident. The method of calculation of the ScE requires that a plateau or scaling region be present for accurate calculations. This is not present in calculation of the ScE on the decimated filtered data. Rather than the calculation of "fractal dimension" which is intended and should be preserved by the calculation when performed on the decimated filtered data, we see instead a complete loss of this information. This is most clearly shown by the curves over time comparing the ScE in unfiltered data at 1000 samples/sec to that on the data at 62.5 samples/sec and filtered to 31.25 Hz (FIGS. 1 and 2). In fact, the ScE is seen to decrease when applied to the decimated filtered data, rather than increase as expected based on the increasing fractal dimension of the signal. This result is actually an artifact of the calculation and quite accidental. This is reflected in the probability density estimates for the ScE when applied to the two groups of data (FIGS. 9 and 10). The peak for the VF samples from time periods less than 5 minutes is no longer at low scaling exponent and high AV regions (FIG. 9) as seen in the original data, but is now at high ScE and high AV values (FIG. 10) in the decimated/filtered data. In stark contrast, the values of the LACadjusted show that this parameter does not change between the original data and the decimated/filtered data (FIGS. 4 and 5). This is also reflected in the probability density estimates comparing the original data (FIG. 7) to the decimated filtered data (FIG. 8).

As described above, the LAC is a quantitative measure of a characteristic (the autocorrelation) of the VF waveform and has proved useful in determining VF duration. The two regions of rapid increase of "LACadjusted" from 0 to 5 minutes and from 8 to 12.5 minutes provide significant determinative features. The calculation is not altered by low sampling rates or by filtering and is therefore a significant improvement when compared to the ScE.

These plots show clearly that the information contained in the LAC, while similar to the ScE is different and novel. In particular, the LAC method is not affected by filtering or sampling rates in the manner that the ScE is. While this is not very important in the laboratory where we can perform experiments without filters and at high sampling rates, this makes it very useful in the environment of current monitors and defibrillators, both of the type used by paramedics and trained hospital personnel, as well as for automated electronic defibrillators (AEDs). These have highly filtered signals at low sampling rates and their algorithms to detect and analyze the heart rhythms have been tuned and optimized to use them. The LAC offers the advantage of allowing the use of current electronic devices without major modifications to calculate a measure useful in objectively measuring the characteristics of the VF waveform described above.

Therefore, I have developed a method to provide a measure of the VF waveform. The information or characteristic or characteristics that are measured are the same or similar to those which are measured by the ScE. The method is distinct, completely different and novel. In particular it is able to measure this information in a heavily filtered VF signal at low sampling rates with a high degree of accuracy. This is a significant improvement and extension of the art in this area of analysis.

Because the appropriate treatment of ventricular fibrillation is strongly dependent upon its duration, the improved devices, systems and methods of the present invention to estimate duration of ventricular fibrillation from a short segment of recorded heart rhythm/ventricular fibrillation provide a significant improvement in the art. Although the methods, devices and systems of the present invention are discussed in terms of a classification system including two classes of ventricular fibrillation (that is, less than 5 minutes duration and greater than 5 minutes duration), a classification system having greater than two classes can be easily developed.

The combination of LAC and AV (or other frequency based measure such as the average frequency as determined by the Fourier transform) in several embodiments of the present invention improves the accuracy of VF duration estimates and provides an improved method of characterization of the VF waveform, to, for example, identify states of the waveform and to identify preferred or optimal treatment methodologies associated therewith. The measured LAC and AV are substantially independent of body habitus, electrode position, electrode conductance, myocardial mass, etc.

The combination of LAC and AV in several embodiments of the present invention improves the accuracy of VF duration estimates and estimates of probability of successful defibrillation. The ability to distinguish VF of less than 5 minutes duration from and VF of greater than 5 minutes duration in signals acquired at low sampling rates and heavily filtered is, for example, a significant advance in the art. Moreover, it is expected that later time periods will be distinguishable using these and related techniques. This ability allows therapies to be developed which can focus on the different phases of VF. These phases have, for example, been divided into the electrical, the circulatory and the metabolic phases. See, for example, Weisfeldt, M L, and Becker, L B, Resuscitation after cardiac arrest: a 3-phase time-sensitive model, JAMA, 288 (23), 3035-8, 2002. Furthermore, the ScE has been shown to be predictive of the probability of successful response to defibrillation attempts in humans, see Callaway, C W, et al., Scaling exponent predicts defibrillation success for out-of-hospital ventricular fibrillation cardiac arrest, Circulation, 2001; 103:1656-61. Since the LAC improves measurements of the same quantities or characteristics measured by the ScE, a combination of the LAC and AV can improve on this predictive ability. The effect of therapies on the myocardium and hence on the VF waveform may be reflected by changes in the LAC and AV so that the timing of defibrillation attempts could be based specifically on the changes in these measures as a response to interventions.

The decrease in LAC over time also supports the possibility that this statistic is a measure of the underlying physiology of the myocardium. The decrease in LAC over time is consistent with the hypothesis that the reduction in energy stores over time results in a reduction in the conduction velocity and signal amplitude, which is then reflected in the decrease in LAC. It is expected that the changes in the LAC which occur over time and follow the same general pattern as are hypothesized for the 3 phases of VF also reflect underlying physiological changes. It is expected that the LAC and the AV (or other frequency based measure), either individually or applied together, will be instrumental in assessing the underlying cardiac physiology of the myocardium and that they will allow the monitoring of patients in VF in a way that is similar to current methods for monitoring the ECG rhythm in patients not suffering from VF. The effect of treatments that are applied, such as chest compressions, ventilations, epinephrine or vasopressin administration, or other treatments to be developed, could then be followed by observing the change in the LAC or the AV (or other frequency measure) or some combination of them.

A treatment methodology, protocol or tool of the present invention (such as illustrated in the figures) can readily be incorporated into an existing defibrillator. In that regard, FIG. 12 illustrates schematically an embodiment of an automated external defibrillator (AED) similar to that disclosed in in U.S. Pat. No. 6,697,671, the disclosure of which is incorporated herein by reference. Another example, of an AED into which the protocols of the present invention can be incorporated is disclosed in U.S. Pat. No. 6,662,046, the disclosure of which is incorporated herein by reference. Commercially available AEDs into which the protocols of the present invention can be incorporated include the LIFEPAK® series of AEDs available from Medtronic Physio-Control Manufacturing Corp. of Redmond Wash.

Although those AEDs are set forth as representative examples of defibrillators into which the protocols of the present invention can be incorporated, one of ordinary skill in the art appreciates that such protocols can be incorporated into virtually any device or system in which heart rhythm is measured.

See FIG. 12: The following is an explanation for the drawing. AED 100 includes a processor (a microprocessor 110 in the illustrated embodiment) which generally controls the operation of the AED 100. The processor used can, for example, be an analog processor or a digital processor, and suitable processors include, but are not limited to: microprocessors, workstations, PC's, hardwired circuitry and the like. Microprocessor 110 is in communicative connection with a user interface system 120, which can include one or more of each of a display, a microphone, a speaker, etc. for the input or output of information. A start/control button 130 and a shock button 140 can also be in operative connection with microprocessor 110.

A memory 150 including a user interface program 160 stored therein is also in communicative connection with microprocessor 110. Memory 150 also has stored therein, for example, as part of or in operative communication with user interface program 160 an operation protocol or program 170 based upon the LAC or based upon the LAC and the angular velocity or other frequency based measure as described above. User interface program 160 can, for example, be formatted as described generally in U.S. Pat. No. 6,697,671. User interface program 160 can, for example, generate visual instructions upon a display of user interface system 120 and/or generate audible instructions transmitted via one or more speakers of user interface system 120. Memory 150 can additionally store a voice recognition software module as known in the art, to enable a user to operate AED 100 and respond to visual and/or audible instructions via voice command rather than using control buttons such as start button 130 and shock button 140.

During operation, the microprocessor 110 analyzes an electrocardiogram (ECG) of a patient using, for example, an automatic heart rhythm algorithm such as disclosed in U.S. Pat. No. 6,697,671 or other algorithm, which is stored in memory 150 to track the heart rhythm of the patient. Currently, such algorithms are functional, for example, to identify whether the patient is experiencing a shockable heart rhythm, such as ventricular fibrillation. Such algorithms are used, for example, in the LIFEPAK®500 defibrillator available from Medtronic Physio-Control Corp. Other such algorithms include those designed to comply with standards promulgated by the Association for the Advancement of Medical Instruments (AAMI). ECG signals analyzed by heart rhythm algorithm 180 are collected by the electrodes 190 and communicated through monitor circuit 200 to an analog-to-digital converter 210 which then passes the digitized signals to microprocessor 110. Under current practice as described, for example, in U.S. Pat. No. 6,697,671, if microprocessor 110 detects a shockable rhythm, microprocessor 110 causes a charging circuit 220 to generate a current causing a storage capacitor (not shown) to charge in preparation for delivery of a defibrillation shock to the patient. When the capacitor is fully charged, and delivery of the defibrillation shock is initiated, a discharge circuit 230 in operative communication with microprocessor 110 and charge circuit 220 discharges the defibrillation shock to electrodes 190 for application of the defibrillation shock to the patient.

The present invention provides a significant advance in the art by providing operation algorithm 170 (which can, for example, operate in conjunction with heart rhythm algorithm 180) based upon the LAC or based upon the LAC and the AV as described above. In accordance with the procedures described above, such an operation protocol can be used to characterize the ventricular fibrillation waveform and/or to determine the state of ventricular fibrillation. The determined character or state of the ventricular fibrillation waveform can be used to determine the likelihood of success of defibrillation to, for example, cause AED 100 to automatically deliver a defibrillation shock if the determined probability is greater than a predefined threshold or to prevent shocking by AED 100 or warn against shocking if the probability of success of a defibrillation shock is less than a defined threshold . If the success of defibrillation is less than a defined threshold, then the AED can also advise the rescuer to begin CPR or an alternative treatment rather than to shock.

When used in connection with monitor defibrillators such as used by highly trained individuals, the treatment protocol of the present invention can provide information as to the duration of ventricular fibrillation or as to the state of ventricular fibrillation to allow, for example, a physician to determine a proper treatment associated with that duration or phase. If, for example, the state of the ventricular fibrillation is consistent with the circulatory phase (as described by Weisfeldt and Becker, see reference above), then CPR may be performed prior to shock. If the ventricular fibrillation is consistent with the metabolic phase, then the advanced life support caregivers can establish IV access and give drugs which would improve or treat the metabolic derangements present prior to shock being delivered. The defibrillator system can also recommend a treatment based upon the probability of a shock or other treatment being successful. A recommended treatment or therapy other than defibrillation (should the probability of success of defibrillation be determined by the system to be below a threshold value) can include, but is not limited to: (1) reperfusion; (2) re-oxygenating the fibrillating heart of the patient; (3) employing a period of cardiopulmonary resuscitation (CPR); (4) employing artificial perfusion; (5) employing one or both of CPR and ventilating the patient and (6) drug administration. Such alternative therapies can be followed by defibrillation, the application and timing of which can be recommended by the system of the present invention based, for example, upon the likelihood of success thereof.

For experienced users, the time course of the character or state of the VF waveform and of the calculated probability of success of a treatment can also be plotted to indicate the progression of the patient's cardiac condition, and to track the response to interventions such as medications or CPR. This relates to the use of the device to monitor ventricular fibrillation and to provide a continuous measure of the state of the myocardium. In this way the measurements may be provided to the experienced user to indicate the effect of interventions as they are delivered. Thus, for instance, the user may use the measure, or some combination of the LAC with the AV or other frequency based measures, to determine when the interventions provided have been sufficient to cause the myocardium to be sufficiently receptive to a defibrillating sock so that there is a high probability of success (above some predetermined threshold). This could be done through any of several methods, including a visual display of a number representing the measure, a bar graph representing the magnitude of the measure, or graph charting the progression of the measure over time, or a bar graph representing the probability of successful defibrillation.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. A method of determining a state of ventricular fibrillation comprising;
    measuring the rhythm of the heart during ventricular fibrillation for a period of time;
    performing calculations with a monitoring device to produce an autocorrelation function of the measured ventricular fibrillation heart rhythm over a given range of lags;
    taking the absolute value of the autocorrelation for each lag;
    determining a first value as a sum of absolute values of the autocorrelation function over the given range of lags; and
    determining the state of ventricular fibrillation based on said first value.

2. The method of claim 1 wherein the first value is a logarithm of the summation of the absolute values of the autocorrelation function over the given range of lags for the period of time, which first value is named the logarithm of an absolute correlation.

3. The method of claim 2 wherein the logarithm of the summation of the absolute values of the autocorrelation function over the given range of lags for the period is calculated on voltage values centered on a mean voltage value for the period.

4. The method of claim 1 further comprising:
   determining a second value related to a frequency spectrum of the ventricular fibrillation heart rhythm for the period of time, the step of determining the state of fibrillation including the step of relating at least one value of the first value and the second value to the state of fibrillation.

5. The method of claim 4 wherein the second value is an area swept out by a structure in a phase space formed from two or three lagged values of the measured ventricular fibrillation heart rhythm.

6. The method of claim 5 wherein the first value is a logarithm of an absolute correlation.

7. The method of claim 6 wherein the determined state of ventricular fibrillation is associated with a probability of success of a mode of treatment of ventricular fibrillation.

8. The method of claim 7 wherein the mode of treatment is defibrillation shock.

9. The method of claim 8 wherein the probability of success of the defibrillation shock is associated with the logarithm of an absolute correlation and the area swept out by the structure formed in the phase space formed from two or three values of the measured ventricular fibrillation heart rhythm.

* * * * *